(12) United States Patent
Stewart et al.

(10) Patent No.: US 9,498,112 B1
(45) Date of Patent: Nov. 22, 2016

(54) LARYNGOSCOPE

(71) Applicants: Brent Stewart, Tampa, FL (US); David Carson, Stuart, FL (US); Stephen Cunningham, Stuart, FL (US); Michael Romeo, Port St. Lucie, FL (US)

(72) Inventors: Brent Stewart, Tampa, FL (US); David Carson, Stuart, FL (US); Stephen Cunningham, Stuart, FL (US); Michael Romeo, Port St. Lucie, FL (US)

( * ) Notice: Subject to any disclaimer, the term of this patent is extended or adjusted under 35 U.S.C. 154(b) by 140 days.

(21) Appl. No.: 14/212,311

(22) Filed: Mar. 14, 2014

Related U.S. Application Data

(60) Provisional application No. 61/800,551, filed on Mar. 15, 2013, provisional application No. 61/798,839, filed on Mar. 15, 2013, provisional application No. 61/799,866, filed on Mar. 15, 2013.

(51) Int. Cl.
| | |
|---|---|
| *A61B 1/267* | (2006.01) |
| *A61B 1/05* | (2006.01) |
| *A61B 1/06* | (2006.01) |
| *A61B 1/00* | (2006.01) |
| *A61M 16/04* | (2006.01) |
| *A61B 1/005* | (2006.01) |

(52) U.S. Cl.
CPC ........... *A61B 1/267* (2013.01); *A61B 1/00052* (2013.01); *A61B 1/0055* (2013.01); *A61B 1/0057* (2013.01); *A61B 1/0058* (2013.01); *A61B 1/00066* (2013.01); *A61B 1/05* (2013.01); *A61B 1/0676* (2013.01); *A61M 16/0488* (2013.01)

(58) Field of Classification Search
CPC ............. A61B 1/00052; A61B 1/0057; A61B 1/267; A61B 1/0055; A61B 1/05

USPC ......................................... 600/194, 188, 196
See application file for complete search history.

(56) References Cited

U.S. PATENT DOCUMENTS

| | | |
|---|---|---|
| 4,218,669 A | 8/1980 | Hitchcock et al. |
| 4,425,909 A | 1/1984 | Rieser |
| 4,483,326 A | 11/1984 | Yamaka et al. |
| 5,138,291 A | 8/1992 | Day |
| 5,183,054 A | 2/1993 | Burkholder et al. |
| 5,297,443 A | 3/1994 | Wentz |

(Continued)

FOREIGN PATENT DOCUMENTS

| | | |
|---|---|---|
| EP | 1167777 A1 | 1/2002 |
| EP | 1174995 A2 | 1/2002 |

(Continued)

OTHER PUBLICATIONS

Boctor, Emad M., et al., "Virtual Remote Center of Motion control for needle-placement robots", Computer Aided Surgery, 2004; 9(5-6): 1-9. Dec. 30, 2004.

(Continued)

*Primary Examiner* — Eduardo C Robert
*Assistant Examiner* — Julianna N Harvey
(74) *Attorney, Agent, or Firm* — McKee, Voorhees & Sease, PLC

(57) ABSTRACT

A system and method of intubating a patient includes an intubating body. A user-control at or associated with the proximal end of the body allows both display of patient oral cavity anatomy and control of orientation of a stylet guide at or near the distal end of the body. The combination assists a user to effectively intubate the patient even if the patient has difficult anatomy.

10 Claims, 33 Drawing Sheets

(56) References Cited

U.S. PATENT DOCUMENTS

| | | | |
|---|---|---|---|
| 5,365,267 A | 11/1994 | Edwards | |
| 5,431,649 A | 7/1995 | Mulier et al. | |
| 5,437,283 A | 8/1995 | Ranalletta et al. | |
| 5,572,999 A | 11/1996 | Funda et al. | |
| 5,722,989 A | 3/1998 | Fitch et al. | |
| 5,904,667 A | 5/1999 | Falwell | |
| 5,962,949 A | 10/1999 | Dhuler et al. | |
| 6,080,151 A | 6/2000 | Swartz et al. | |
| 6,149,664 A | 11/2000 | Kurz | |
| 6,461,242 B2 | 10/2002 | Takeda et al. | |
| 6,468,203 B2 | 10/2002 | Belson | |
| 6,469,415 B2 | 10/2002 | Jerman et al. | |
| 6,498,711 B1 | 12/2002 | Sharma | |
| 6,529,765 B1 | 3/2003 | Franck et al. | |
| 6,652,453 B2* | 11/2003 | Smith | A61B 1/00052 600/188 |
| 6,770,027 B2 | 8/2004 | Banik et al. | |
| 6,858,005 B2 | 2/2005 | Ohline et al. | |
| 6,965,394 B2 | 11/2005 | Gutta et al. | |
| 7,169,155 B2 | 1/2007 | Chu et al. | |
| 7,225,012 B1 | 5/2007 | Susil et al. | |
| 7,261,686 B2 | 8/2007 | Couvillon, Jr. | |
| 7,282,051 B2 | 10/2007 | Rioux et al. | |
| 7,419,489 B2 | 9/2008 | Vanney et al. | |
| 7,500,948 B2 | 3/2009 | Cantrell | |
| 7,578,786 B2 | 8/2009 | Boulais et al. | |
| 7,662,128 B2 | 2/2010 | Salcudean et al. | |
| 7,695,433 B2 | 4/2010 | Simons | |
| 7,924,514 B2 | 4/2011 | Chou | |
| 8,052,684 B2 | 11/2011 | Wang et al. | |
| 8,083,879 B2 | 12/2011 | Swinehart et al. | |
| 8,125,755 B2 | 2/2012 | Garcia et al. | |
| 8,182,418 B2 | 5/2012 | Durant et al. | |
| 8,223,461 B2 | 7/2012 | Huang et al. | |
| 8,280,561 B2 | 10/2012 | Griggs et al. | |
| 8,361,090 B2 | 1/2013 | Belson | |
| 2002/0080248 A1* | 6/2002 | Adair | A61B 1/00096 348/230.1 |
| 2004/0251439 A1 | 12/2004 | Yee et al. | |
| 2005/0018042 A1 | 1/2005 | Rovegno | |
| 2005/0055019 A1 | 3/2005 | Skarda | |
| 2008/0177147 A1 | 7/2008 | Simons | |
| 2008/0177362 A1 | 7/2008 | Phillips et al. | |
| 2008/0221591 A1 | 9/2008 | Farritor et al. | |
| 2010/0261967 A1 | 10/2010 | Pacey et al. | |
| 2010/0261968 A1* | 10/2010 | Nearman | A61B 1/00041 600/188 |
| 2011/0028790 A1* | 2/2011 | Farr | A61B 1/00052 600/187 |
| 2011/0106101 A1 | 5/2011 | Tortonese et al. | |
| 2011/0144436 A1 | 6/2011 | Nearman et al. | |
| 2011/0178373 A1 | 7/2011 | Pacey et al. | |
| 2011/0201886 A1 | 8/2011 | Gumbs et al. | |
| 2011/0270038 A1 | 11/2011 | Jiang et al. | |
| 2011/0319718 A1 | 12/2011 | Hakanen et al. | |
| 2013/0123760 A1 | 5/2013 | Spaide | |
| 2013/0274556 A1* | 10/2013 | Nearman | A61B 1/267 600/187 |
| 2013/0310650 A1* | 11/2013 | Hales | A61B 1/267 600/188 |

FOREIGN PATENT DOCUMENTS

| | | |
|---|---|---|
| EP | 1223346 A1 | 7/2002 |
| EP | 1515637 B1 | 6/2003 |
| EP | 2508120 A1 | 10/2012 |
| WO | 2009015396 A2 | 1/2009 |

OTHER PUBLICATIONS

Pham, M.T., et al., "A Biomimetic Steering robot for Minimally invasive surgery application", Advances in Robot Manipulators, In-Tech (Ed.)(2010), pp. 1-25. Dec. 30, 2010.

ZEFON International, "Extech BR250 Video Borescope/Wireless Inspection Camera", http://www.zefon.com/store/extech-br250-wireless-inspection-camera-video-borescope.html [retrieved from internet Nov. 26, 2012.

* cited by examiner

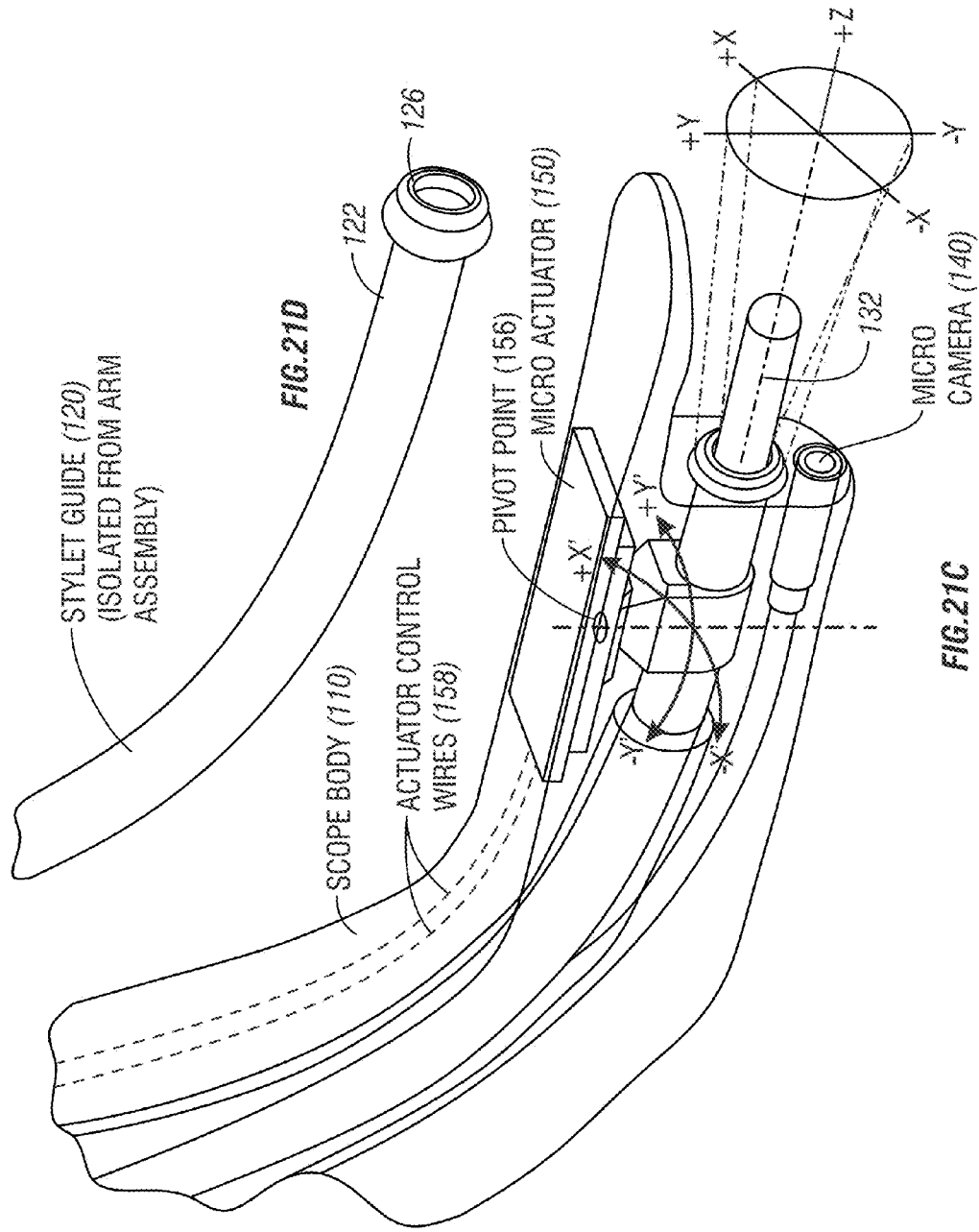

LARYNGOSCOPE

CROSS-REFERENCE TO RELATED APPLICATIONS

This application claims priority from U.S. Provisional Application Ser. No. 61/798,839 filed Mar. 15, 2013; 61/799,866 filed, Mar. 15, 2013; and 61/800,551, filed Mar. 15, 2013, the entire contents of each of which are hereby incorporated herein in their entirety by reference.

BACKGROUND OF THE INVENTION

A laryngoscope is a device for viewing the vocal cords in a patient's airway. Once visualized, the operator can place an endotracheal tube through the opening between the vocal cords, and into the trachea. Mechanical or spontaneous ventilation then occurs through the endotracheal tube. An example of a laryngoscope is described and illustrated in U.S. Pat. No. 4,425,909, incorporated by reference herein. U.S. Pat. No. 4,425,909 shows the basic operation of a laryngoscope, which is well-known to those skilled in this technical art, so those background details will not be repeated here.

A variety of modifications to the standard laryngoscope have been attempted. The modifications are done to better facilitate placement of a tube in a patient with difficult anatomy. An example of one approach to improving airway management by an articulable laryngoscope blade can be seen in U.S. Publication No. 2011/0144436, incorporated by reference herein. Current modifications typically involve the use of a video camera to better view the internal anatomy on a display screen. Examples of a video-supplemented laryngoscope are described in US2011/0270038, US2010/0261967, and US2011/0319718, each of which is incorporated by reference herein.

The typical patient is muscle-relaxed (paralyzed) with drugs that prevent spontaneous breathing and allow for relaxed oropharyngeal muscles to optimize intubation. In such a circumstance, the patient is completely dependent upon the operator to secure the airway. Failure to secure the airway can easily result in death.

Therefore, the need for tools and instruments to accomplish such intubation is very important. The need for improvement in this technical art continues. It would be beneficial to intubate the trachea with the same device that visualizes the trachea and which allows highly manipulatable navigation therethrough.

Many current products are limited by either visualization of the cords only or employ only a static guide to endotracheal tube placement. In the second case, if the operator is unable (or the patient's anatomy is difficult) to center the cords on the monitor screen, the operator is unable to actually place the endotracheal tube, no matter that he/she can still see the target on a monitor screen.

The present invention incorporates the ability to see the cords, adjust a guiding stylet toward the cords, and advance the stylet toward and/or pass through the tracheal carina to place the endotracheal tube.

SUMMARY OF THE INVENTION

The present invention has the ability to guide or actuate a stylet for highly flexible, guided placement of the endotracheal tube.

There is a difference between visualizing the vocal cords and actually intubating the trachea. A difficult airway will still be difficult to intubate if the operator cannot effectively place an endotracheal tube, even if the vocal cords are visible.

According to an aspect of the invention, a laryngoscope instrument or system includes a body with a stylet guide or pathway, camera vision at or near the distal end of the body, camera view display at or near the proximal end of the body or the user, and highly manipulatable control of stylet exit and trajectory at and from the distal end of the body by an actuator manipulating the stylet guide through instruction from a manually operable user control at or near the proximal end of the body. The instrument or system allows both visualization of relevant internal patient air way anatomy and a high degree of control of endotracheal tube placement from outside the patient.

According to another aspect of the present invention, a laryngoscope includes an intubation body having a curved shape between proximal and distal ends, a proximal handle that houses a control system, and a distal end effector or working end which can change shape or orientation based on the control system and serves as a stylet guide. The change of shape of the distal working end in effect changes the exit and trajectory of a stylet that can be threaded through at least a portion of the intubation body and the working end. A set of elongated and flexible wires extends through the laryngoscope intubation body between the control system and the end effector. The wires are elongated and flexible but are resistant to longitudinal deformation in compression or tension. Thus, pushing or pulling on one end of a wire will result in a commensurate movement of the other end of that wire. A user interface allows the user to manually indicate a change in orientation of the end effector. The manual indication is translated by the control system to a correlated actual change of distal end orientation by manipulating the wires or rods. Examples of a user interface is a tactile "joystick" or accomplished mechanically through push-button, slide, rotary, or analogous user interface. Another example would be a touchscreen. Change in distal end orientation can be in multiple directions and trajectories and at least up, down, left and right and essentially is a movable stylet guide. One example of the foregoing could be a self-contained laryngoscope including both on-board electrical power for actuation, camera, and illumination sources and an on-board display so the user can view anatomy of the patient at the distal working end. A controller or circuit board can instruct the operation of the articulating guide tip. The assembly allows visualization of internal airway anatomy of the patient and then articulation of the stylet guide to selectively alter the angle of exit of a stylet from the distal end of the laryngoscope body distal end.

According to another aspect of the invention, the laryngoscope assembly described above could be utilized with a user interface that could allow instruction of the articulating guided tip. In one example the user-interface can be an attached and removable touchscreen. Another example would be an iPad or touch screen monitor/television panel. These interfaces can be either wired, wireless or Bluetooth.

According to a still further aspect of the invention, a laryngoscope assembly comprises a laryngoscope body having a longitudinal bore or passageway between a distal end opening and a proximal end opening, a stylet guide positioned along the bore of the laryngoscope body and having proximal and distal open ends, a digital or fiber optic camera at or near the distal end of the stylet guide, and an articulating guide tip operatively associated with the distal end of the stylet guide. At least the distal end of the stylet guide can be articulated in at least two degrees freedom of movement by the articulating guide tip. A programmable controller can instruct operation of the articulating guide tip. The assembly allows visualization of internal anatomy of the patient and articulation of the stylet guide to selectively alter the angle of exit of a stylet from the distal end of the laryngoscope body distal end, or angle or shape of the distal end of that tip. This allows fine adjustment of the tip relative to the patient's anatomy.

According to another aspect of the invention, the laryngoscope assembly described above could be utilized with a user interface that could allow electrical or electronic instruction at the articulating guide tip to cause automatic (as opposed to manual) adjustment of the tip while the laryngoscope body is in place in the patient's throat. In one example the user-interface can be a touchscreen. The touchscreen could display both the field of view of the camera (and thus the patient's internal anatomy) and convert a tactile touch on the screen location by the user to an instruction of how much and in what direction the articulating guide tip should adjust the angle of the stylet relative to the longitudinal axis of laryngoscope body at its distal end or relative to some other reference. By appropriate calibration, tactile input to the touchscreen can correspond to how much and what direction of stylet guide or stylet angular adjustment is automatically affected by the articulating guide tip. In this way, the physician can view the internal anatomy on the touch screen and touch where the stylet should go. The system then automatically instructs the articulating guide tip to set a corresponding angle of the distal end of the stylet guide or stylet so that the stylet, threaded through the stylet guide from proximal to distal end, can be axially extended out of the distal end of the stylet guide in a trajectory either influenced by the angle of the distal end of the stylet guide or the angle of the stylet itself (if it is adjustable in shape) to result in proper placement of the distal end of the stylet relative to the patient's anatomy.

According to other aspects of the invention, the precise way in which the stylet can be guided in different selectable exit paths from the distal end of the laryngoscope body can vary. In one example, the stylet guide distal end can be adjusted in angular orientation, which would influence a change in the exit path of the stylet from the stylet guide. Another example is to construct the stylet itself in a way that its angle or shape can be adjusted by remote control. Methods of actuation can include proximally manipulated guide wire(s), proximally or distally located solenoid(s), proximally or distally located shape memory alloy (SMA) wire, proximally or distally located electric motor(s). Similarly, there are different user-interfaces, articulating guide tips, image transfer devices, actuators and other components that are possible.

According to other aspects of the invention, a method of laryngoscopy includes inserting a laryngoscope with an internal stylet guide into proper general placement in a patient determining if there is offset between a reference projection of its longitudinal axis from its distal end and a desired projected path through the patient's anatomy and if there is an offset automatically altering the stylet guide to the desired projected path. The stylet guide can be a tubular member which is adjustable in orientation relative the scope or a distal end of the scope which can be adjusted in orientation.

According to other aspects of the invention, a system of one of the laryngoscope assemblies discussed above can be in combination with a control station including a touchscreen or other user-interface and other components and software to effectuate user instruction of articulation of the distal end of the stylet guide and allow a user visualization of placement of the distal end of the laryngoscope and adjustment of the path of exit of a stylet from the stylet guide.

According to other aspects of the invention, the specific shape of the laryngoscope handle and blade can vary according to need or desire. A basic adaptation to suit the desires of the manufacturer would not affect the functionality of the present invention. While a sturdy, durable, lightweight material would be ideal in this design, the specific materials do not significantly affect the implementation of the present invention. The design could involve disposable or non-disposable materials. Generally, the endotracheal tube is disposable. The body of the instrument could likewise be disposable.

BRIEF DESCRIPTION OF THE DRAWINGS

FIGS. 21A-C are different perspective views of a laryngoscope assembly according to second exemplary embodiment of the present invention. FIGS. 21A-C are in wire-frame form, showing both external and internal parts. FIG. 21A is the entire laryngoscope body and associated internal components. FIGS. 21B and C are enlarged view of just the distal end of the embodiment of FIG. 21A. FIG. 21D is an isolated view of just the stylet guide of the assembly of FIGS. 21A-C. In this embodiment, a flexible tube, called a stylet guide, extends through the instrument body from proximal to distal end. An actuator changes the orientation of the distal end of the stylet guide to change the exit point and trajectory of a stylet threaded through the tube comprising the stylet guide.

FIG. 26A includes a diagrammatical depiction of a control/processing system that allows a physician to view internal patient anatomy once the laryngoscope body is inserted (on a touch screen), and instruct adjustment of the angle of the stylet guide distal end (to effect the exit path of a stylet pushed out that end) by simply touching a target position on the touch screen.

DETAILED DESCRIPTION OF EXEMPLARY EMBODIMENTS

A. Overview

For a better understanding of the invention, specific embodiments will now be described in detail. It is to be understood these are not inclusive or exclusive of different forms or variations the invention can take but are merely illustrative of several of those forms.

As described above, the invention relates to a laryngoscope assembly and system, and method of using the same to intubate a patient.

Several features of the exemplary embodiments include a camera and illumination system carried on the assembly that allows field-of-view visualization at the distal end of the assembly to be displayed on a digital or video display. Examples of laryngoscopes having that capability are shown and described at U.S. Published Applications US 2011/0270038, US 2010/0261967, and US 2011/0319718. Each of those discloses how a visualization of the area around the distal end of the laryngoscope can be displayed for the user. US 2011/0270038 discloses a video display attached directly to the laryngoscope. The others show displays that are separated from the scope. Each of these references provides details about how such an optical system can be made and used. Further detail will not be given here. Each of these references is incorporated by reference herein.

The examples given below illustrate that the general principles and aspects of the invention can be implemented in various ways. A unifying concept of these embodiments is the combination of:

a. an intubating body which can be positioned in and through the oral cavity and to the larynx of the patient;
  b. a camera lens and illumination source output at or near the distal end of the body to provide an image of the patient's anatomy at and around the present position of the distal end of body;
  c. a means of adjusting in multiple directions the trajectory of a stylet threaded through and then out of the body distal end to allow remote control of navigation of the distal end of the stylet relative to the patient's anatomy, including while viewing the camera image of the patient's anatomy.

Advantages of the invention include, without limitation, providing a means for an anesthesiologist/physician who is struggling with a difficult patient airway use of an instrument to articulate the stylet, as the vocal cords almost always appear up, which is challenging, as the patient's jaw bone, tongue, and other soft tissues provide resistance to that motion. Thus, the anesthesiologist/physician is able to angle upward, left, right and downward for fine positioning.

B. Exemplary Embodiment 1

Figure 1A:
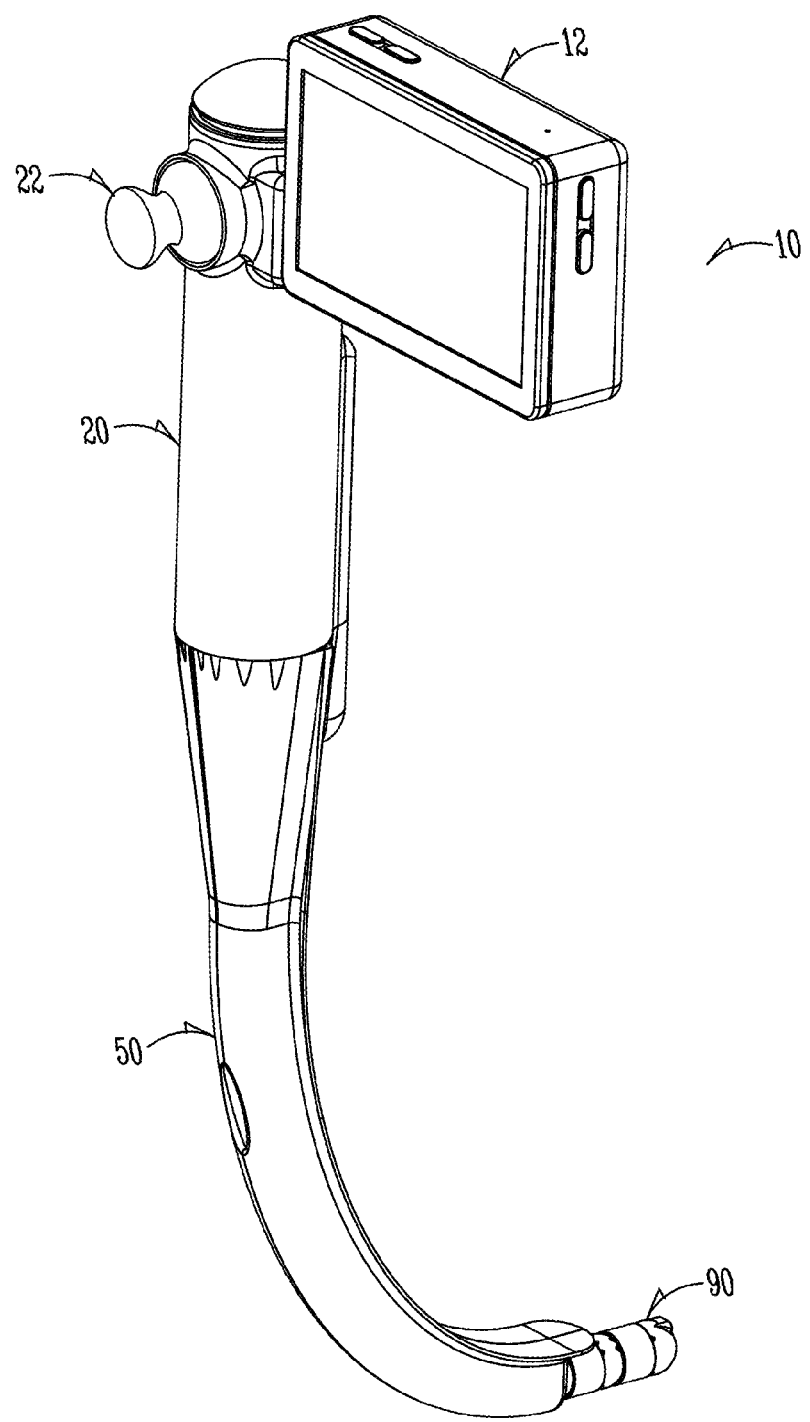
FIG. 1A is a high angle, right side, perspective 3D model view of a first exemplary embodiment according to the invention.
Figure 1B:
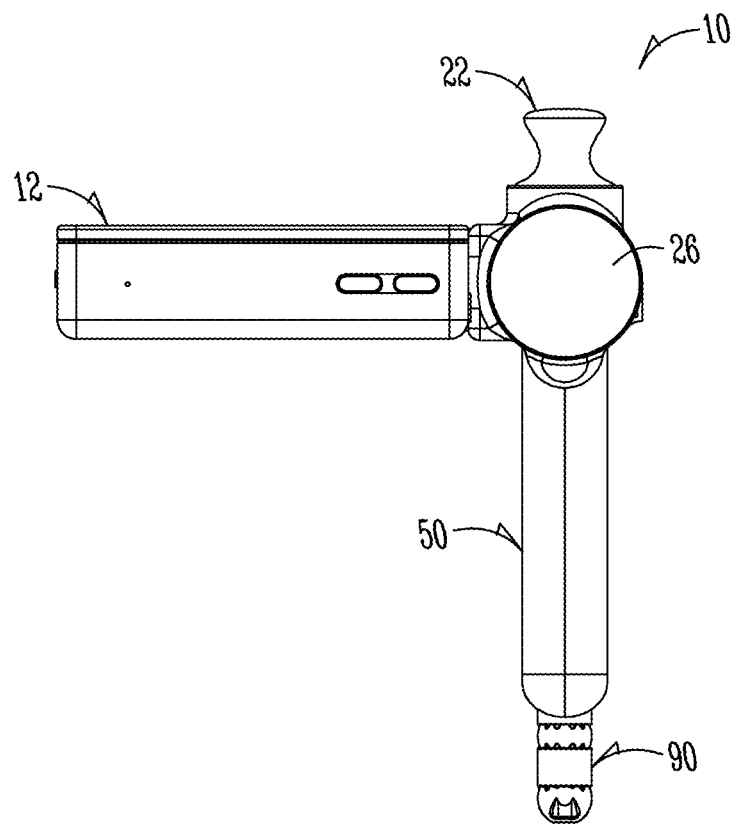
FIGS. 1B-E are top, back, right side, and front plan views of FIG. 1A respectively.
Figure 1C:
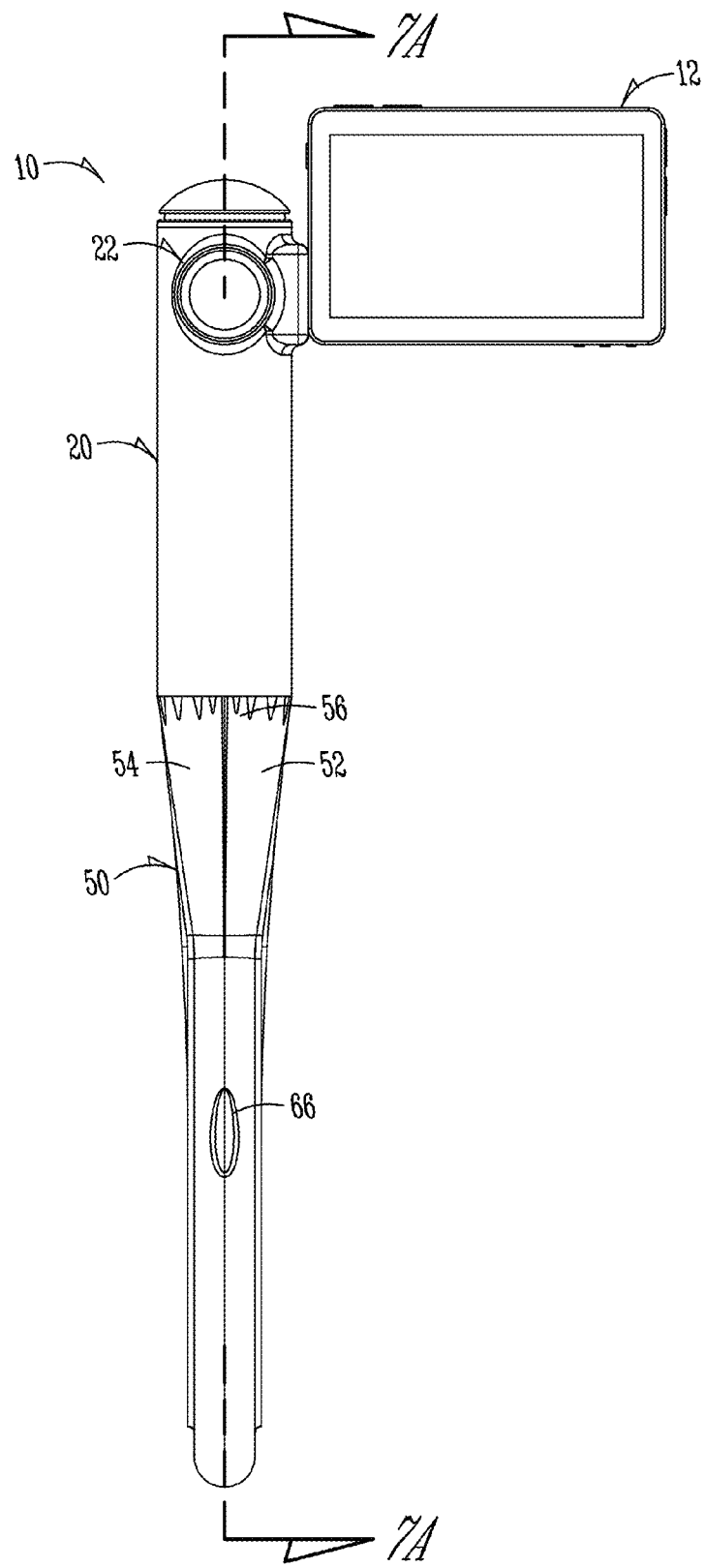
Figure 1D:
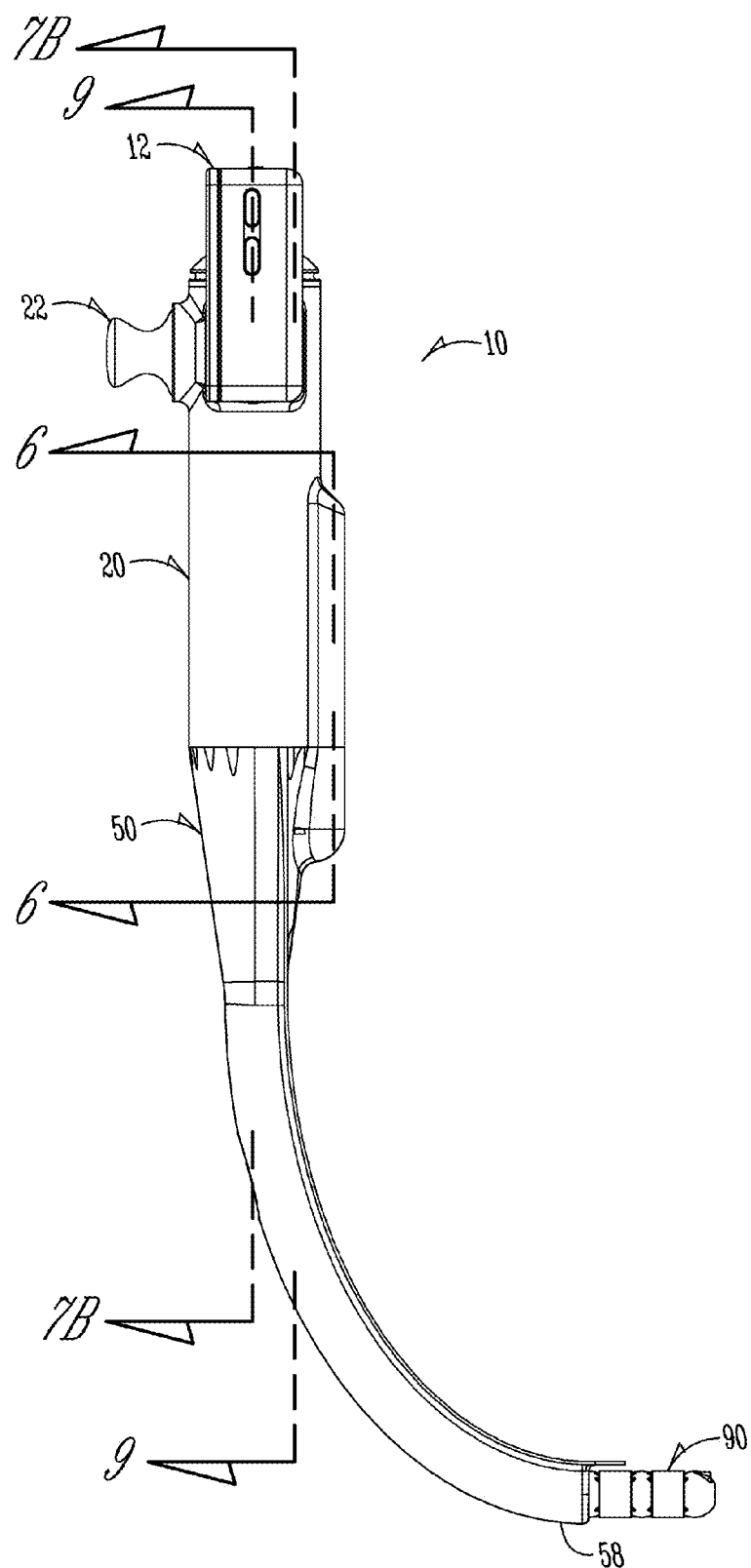
Figure 1E:
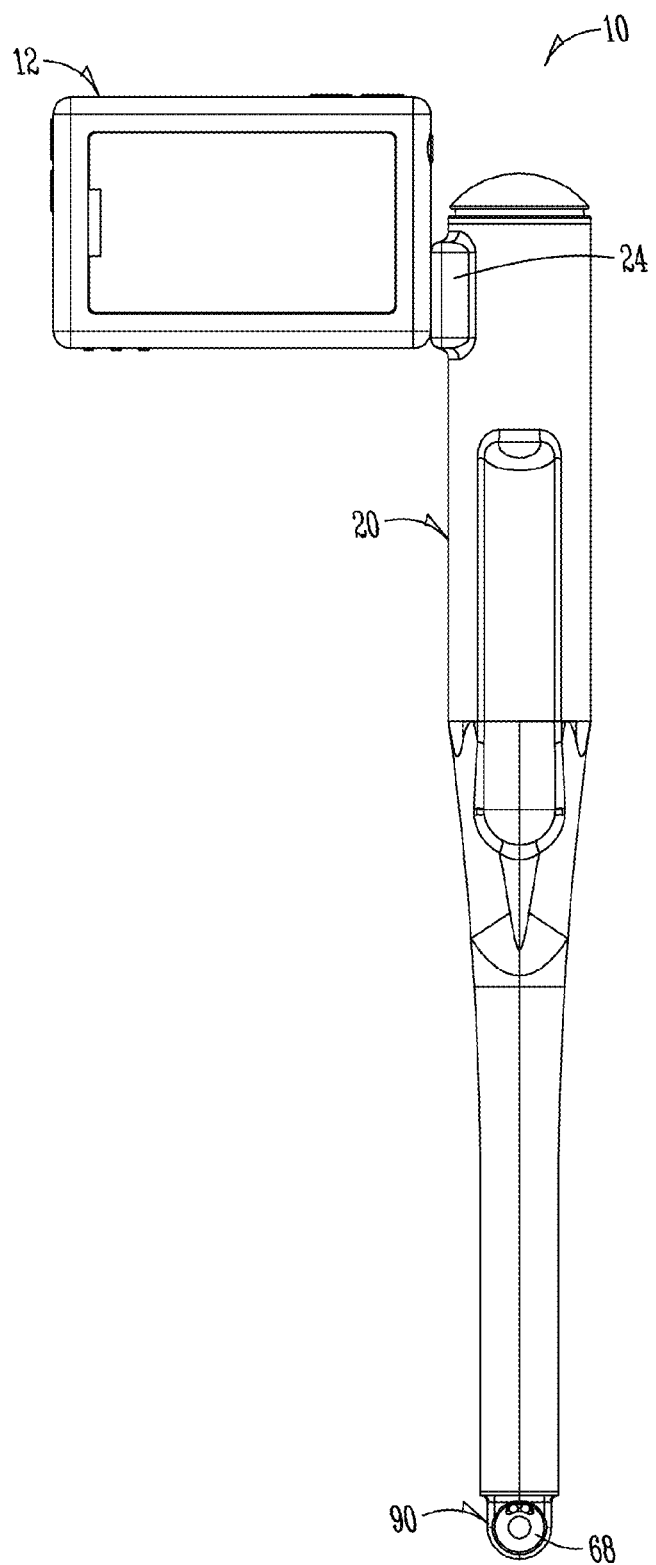

A first embodiment of a form the invention can take is shown in assembled form in FIG. 1A. It is self-contained in the sense an on-board electrically actuated system can change orientation of the working distal end by actuators inside the device along with a battery power source. The working distal end essentially functions as a manipulatable stylet guide. A manually operable joystick is integrated into the device. A display screen also allows the user camera-vision at the distal end by an onboard camera and illumination source that, through fiber optics, have a field of view that is illuminated at the distal end of the working end.

The device can be held and operated by one hand. It allows insertion of the distal end into the patient, view on a display screen of the anatomy around and ahead of the distal end, and then highly controllable manipulation (e.g. by the thumb of one hand gripping the device) of orientation of the working end of the device to place the angular orientation of that distal end as desired. This adjustable orientation of the distal end allows user control of the exit trajectory of a stylet out of that adjusted distal end to allow a high degree of user-control of navigation of the stylet relative to the patient's airway anatomy.

A stylet channel through the intubation body of the device allows the user to thread a stylet through and out of the body at a trajectory set by the orientation of the distal end or working end and towards the trachea of the patient. That stylet can then be used to guide an intubation tube along that same trajectory.

1. Apparatus

FIG. 1A shows instrument or device 10 in assembled form. It also shows the device can be substantially self-contained. The form of device has an integrated and aesthetically pleasing appearance. FIGS. 1B-E show assembled instrument 10 from various view angles.

Figure 2:
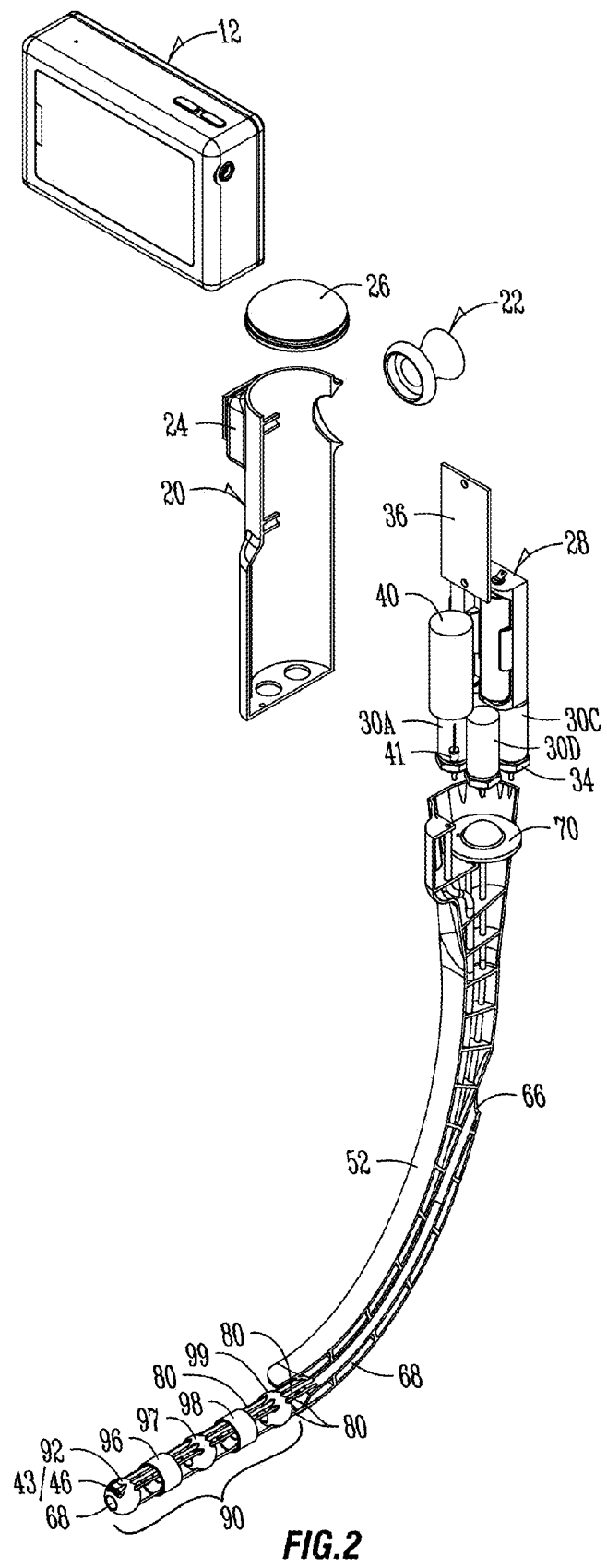
FIG. 2 is a partly exploded view of FIG. 1A with portions (left side handle and intubating body housing halves) removed and not shown.

As shown in FIG. 2, (a) an LED 41 and associated fiber optic cable(s) and guide tube through body 50 to lens or window 46 in distal end 90, (b) micro camera 40 and associated fiber optic cable(s) and guide tube, (c) wires 80 and associated wire guide tubes for mechanical actuation of distal end 90, (d) a distal tip sub-assembly 90 containing the LED fiber optic cable(s) and camera coherent fiber optic cable(s), vertebral bodies 96 and 98, intervertebral joints 92, 97, and 99, (e) stylet entry point 66 of the intubating body 50, (f) gyro disk 70, (g) linear solenoids 30 (sealed, "push" style), and (h) handle body 20 with AA battery holder 28, PCB solenoid controller 36, LED monitor connection point 24, joystick 22, cap 26, and the interactive LED monitor 12, are primary components of what will sometimes be called Guided Trachea Intubating Device 10.

Figure 4A:
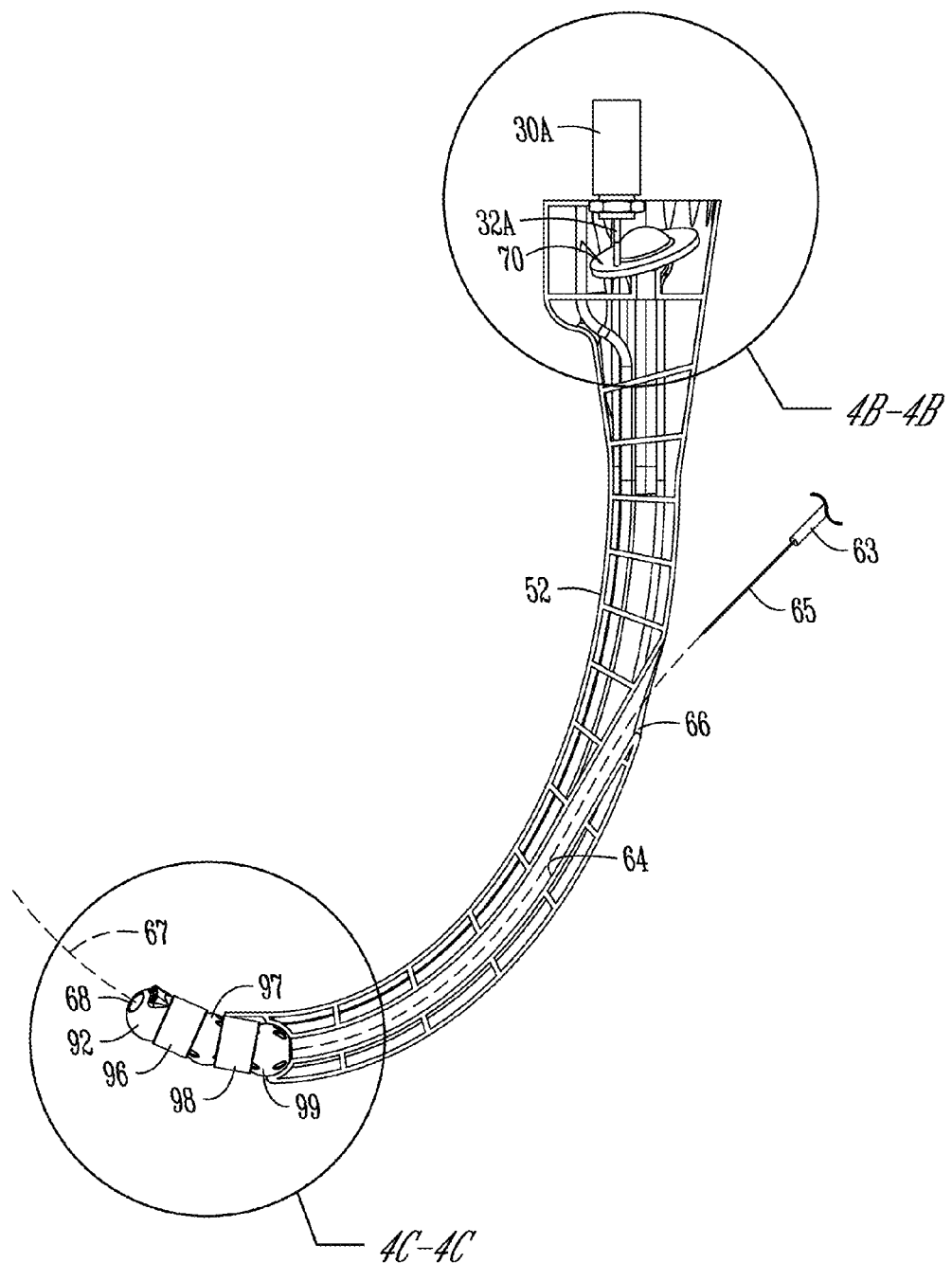
FIG. 4A is a detailed, right side 2D model side elevation view of most of the body and mechanical interface defining the actuation of the articulating tip of FIG. 2.

Providing more detail of the mechanical components of the invention, referring to FIGS. 2 and 4A and B, there is shown gyro disc 70 which is seated on a radial point 76 molded into the intubating device. Micro wires/cables 80A-D (located 90 degrees from one another) attach to the gyro disk in four locations and run linearly from gyro disk 70 to articulating guide tip 90 through sheathed tubing features in the intubating device. Contraction of the micro-wires 80 create "bend" or curve at tip 90 in two degrees axial articulation 360 degrees in the direction of whichever wire 80 is shortened via actuation. Four electric solenoids 30 and mounting nuts 34 seated in the handle body 20 interact with gyro disc 70 (located 90 degrees from one another) to "push" or "pull" on at least one opposing cable 80 and articulate tip 90 in an opposing direction. Referring to FIGS. 4A-C and 8, there is shown an LED fiber optic light array 41/45 to safely transmit light from handle assembly 20 to the distal tip 90, at the superior and anterior tips. A polished lens 46 may be required to focus the light. The mechanical wires/cables 80 attach to distal tip 90 and pass through the vertebral bodies and intervertebral joints of tip 90 up to gyro disk 70 at the superior end 56 (FIG. 1C) of intubating device or body 50. Alternatively, Shape Memory Alloy (SMA) wires may be used. Distal tip 90 (at the inferior end 58 of body 50) houses the lenses 46 and 43 for LED fiber optic light array 45 and micro camera coherent fiber optic array 42.

Many of these components may be made from medical grade engineering plastic as injection molded parts which may be any color and may be autoclavable other materials such as aluminum alloys. Some parts may be medical grade stainless steel or ASTM F-75 cobalt chrome alloy. Vertebral bodies 96 and 98 which provide articulation through intervertebral joints 92, 97, and 99 of distal end 90 by means of mechanical wire/cables 80 may be made from medical grade engineering plastic as injection molded parts which may be any color and may be autoclavable other materials such as aluminum alloys. Medical grade stainless steel or ASTM F-75 cobalt chrome alloy may be utilized.

Handle/Display

Figure 5:
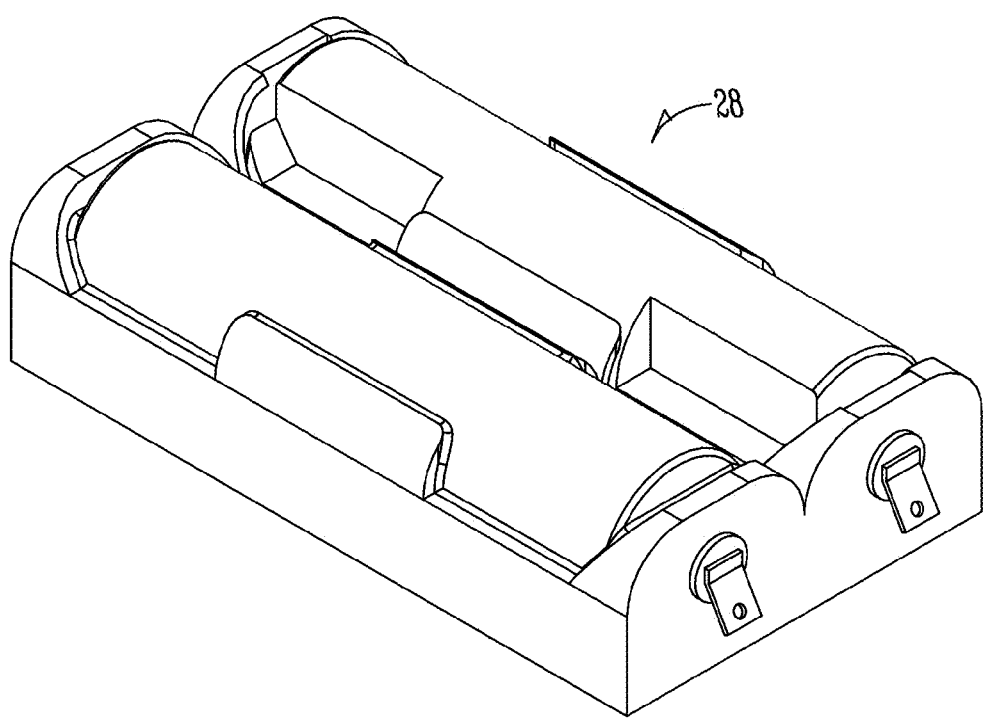
FIG. 5 is a perspective in isolation of a battery pack in the handle of FIG. 1A.
Figure 6:
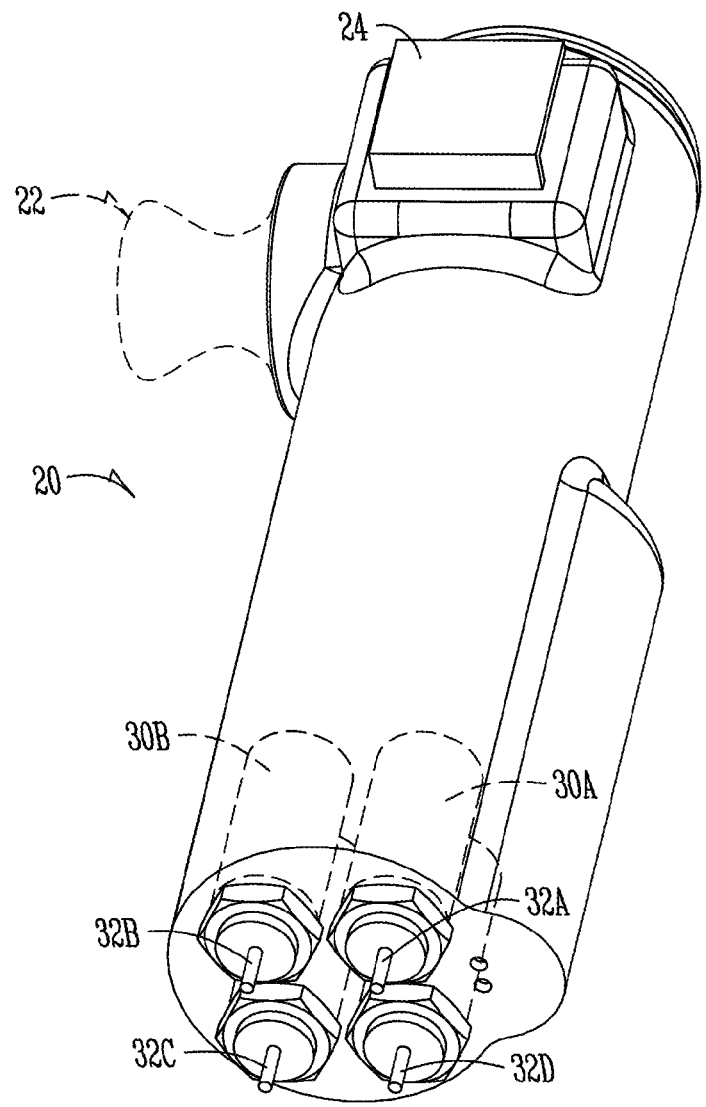
FIG. 6 is a perspective of the detachable handle of FIG. 1A.

Handle 20 can be comprised of two halves that when combined produce the basic structure of FIG. 6. Joystick 22 would be pivotally mounted and extend into the interior. Monitor mount 24 is integrated along one side. Cap 26 would seal off the top and allow battery pack 28 (FIG. 5) to be accessed. Solenoids 30 as well as circuit board 36 can be built into handle 20.

Handle body 50 (right/left) can be made from medical grade engineering plastic as injection molded parts which may be any color and may be autoclavable other materials such as aluminum alloys, medical grade stainless steel or ASTM F-75 cobalt chrome alloy may be utilized. Joystick may be made from medical grade engineering plastic as injection molded parts which may be any color/texture and may be autoclavable. Cap 26 can be made from medical grade engineering plastic as injection molded parts which may be any color and may be autoclavable other materials such as aluminum alloys, medical grade stainless steel or ASTM F-75 cobalt chrome alloy may be utilized.

A display such as interactive LED monitor 12 (e.g., SoundGraph FingerVU 436 USB 4 inch Touch Screen Monitor available from SoundGraph, Inc., 4F, Sewoon B/D, 57-12 Nonhyon-dong, Gangnam-go, Seoul, Korea 135-010) can be mounted on handle portion 20 and operatively connected to camera 40. Handle 20 can be detachable and include AA battery pack 28 (FIG. 5) and the set of solenoids (sealed push) 30 (FIG. 2) (e.g. see U.S. Pat. No. 4,218,669 incorporated by reference herein). Additionally, joystick 22 can be operatively mounted in handle 20 such that handle 20 could be held in one hand in the orientation of device 10 in FIG. 1A and joystick 22 operated by a thumb from that same hand. AA battery holder 28 may be removable for ease of use.

Joystick 22 can have an interface circuit 36 (FIG. 2) which would transduce the angular position of joystick 22 and convert that into electrical instructions to solenoids 30 as will be described below. Basic operating principles of a thumb or finger controlled joystick can be seen at U.S. Pat. No. 6,461,242 which is incorporated by reference herein. Basic principles of converting a manual control (including joystick or similar) to operation of a set of actuators can be seen at U.S. Pat. No. 8,280,561 which is incorporated by reference herein. Essentially, movement of joystick 22 will cause a corresponding movement of working end 90 of device 10. For example, if joystick 22 is moved slightly upward when device 10 is in the orientation of FIG. 1A, tip 90 would move slightly upward. If joystick 22 is moved fully upward, tip 90 would move fully upward in a calibrated additional amount within a range of possible movement of end 90.

As can be appreciated, downward movement of joystick 22 results in downward movement of end 90. Left or right lateral movement results in left or right movement of tip 90. And, thus, any direction in between up, down or lateral in either direction, would be calibrated and cause corresponding movement of tip 90. In this manner, one hand control of the orientation of tip 90 relative to instrument 10 can occur.

Figure 20:
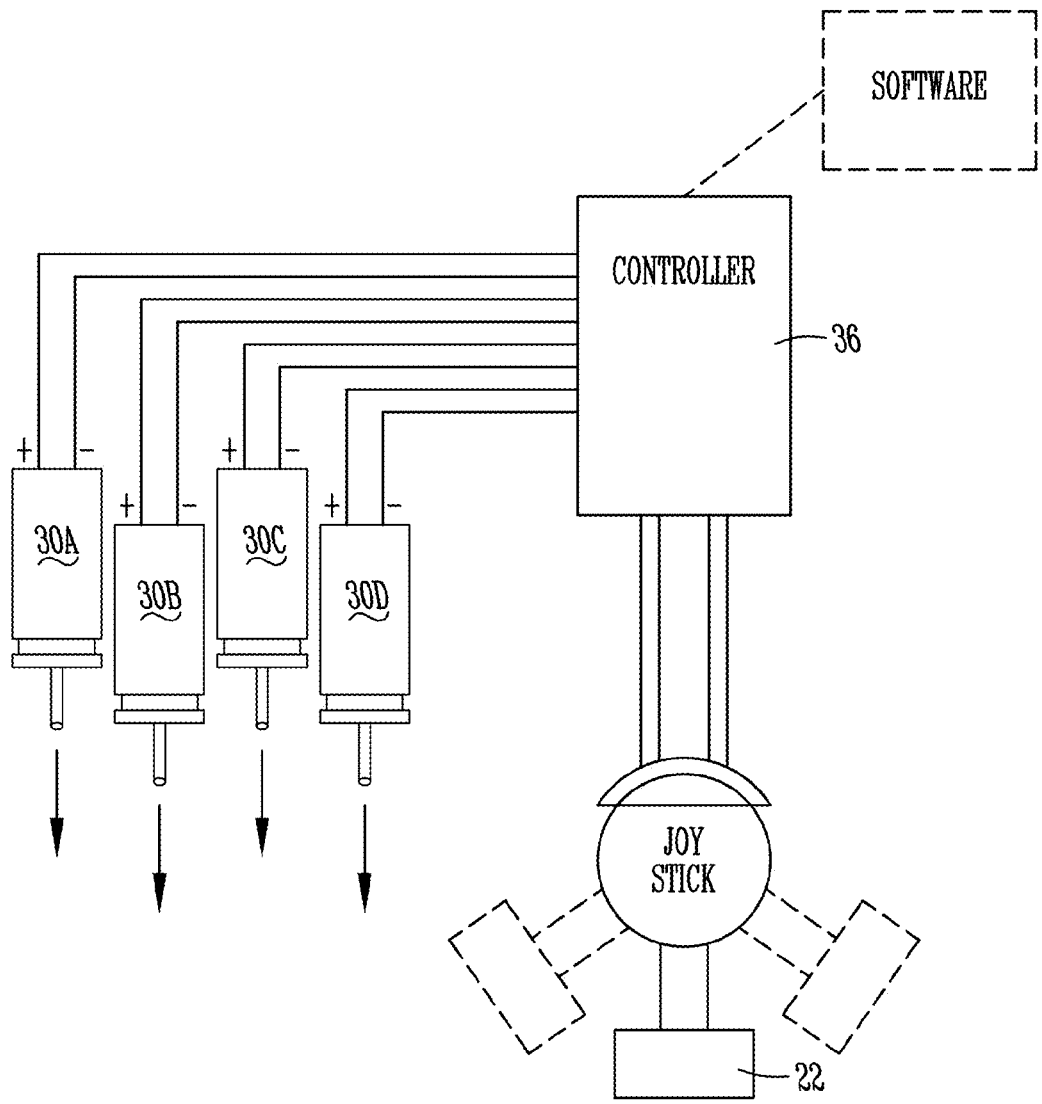
FIG. 20 is a diagrammatic view of the electrical connection and control of solenoids according to this embodiment.

FIG. 20 illustrates diagrammatically the electrical circuitry of device 10. Joystick 22 would have an interface via controller board or circuit 36 which has components programmed to transduce direction and amount of movement of joystick 22 into how much and which solenoid 30A-D should be activated. If the joystick 22 is used for control, commercially available interfaces for circuitry 36 are known. One example is model SC5 Five-channel solenoid controller/driver available from RW Automation, LLC 19992 Buckhaven Ln., Saratoga, Calif. 95070.

Camera/Illumination Source

Figure 8:
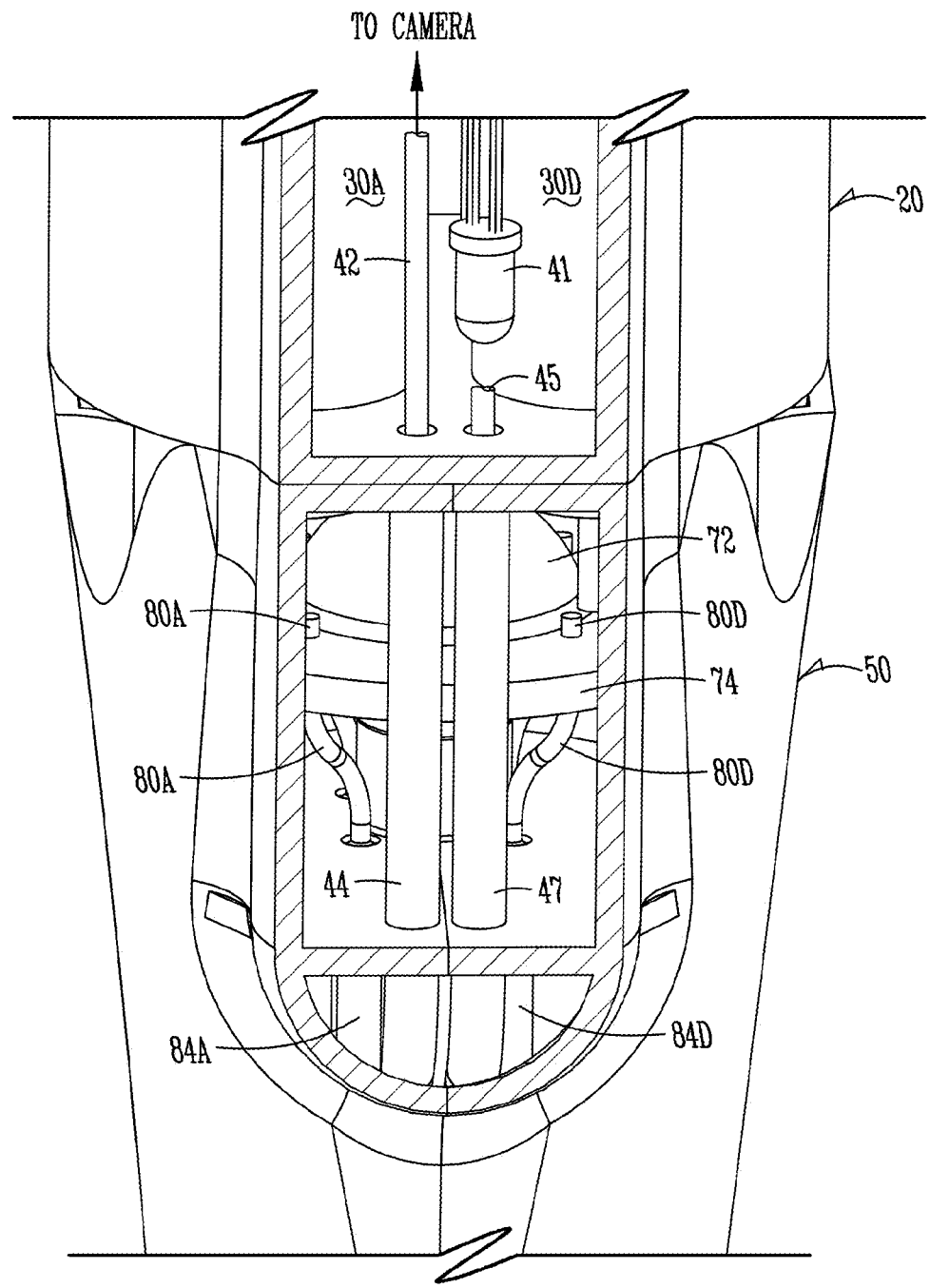
FIG. 8 is an enlarged sectional view showing internal assembled components in the handle of the device of FIG. 1A (see line 8-8 of FIG. 1D).

FIG. 8 shows in detail the positioning of the LED 41 and its fiber optic 45, as well as the fiber optic 42 for the camera 40 (see FIG. 2). Guide tubes 44, 47 are also indicated.

LED 41 safely transmits light from the control module into distal tip 90 by transmission through fiber optic cable. Micro camera 40 safely transmits images from distal tip 90 to the proximal "control module" in handle 20 by transmission through a coherent fiber-optic core which magnifies/displays image on either the hand-held, wired or wireless monitor (see FIG. 3).

Micro camera 40 in handle 20 would be operatively connected to a coherent fiber optic array 42 (see FIG. 8) that extends to lens 43 at the very distal part of distal end 90 to capture a field of view at lens 43. Similarly, LED source 41 and associated fiber optic 45 (FIG. 8) would extend to end 90 and project illumination of at least a portion of the field of view of camera 40. These components can be selected according to need or desire to give the user adequate vision of patient anatomy at display 12 (and/or tablet 14 and monitor 16 of FIG. 3).

Monitor connection point 24 provides physical connection to interactive LED monitor 12.

On-board microcamera 40, LED illumination source 41, and fiber optics (42 and 45) can be guided through tubes 44 and 47 respectively along body 50 and through the working end 90 to sealed windows or lenses 43 and 46 (see FIG. 14) to provide a field of view and illumination at that distal end. Such components are commercially available.

Optional Auxiliary Components

Figure 3:
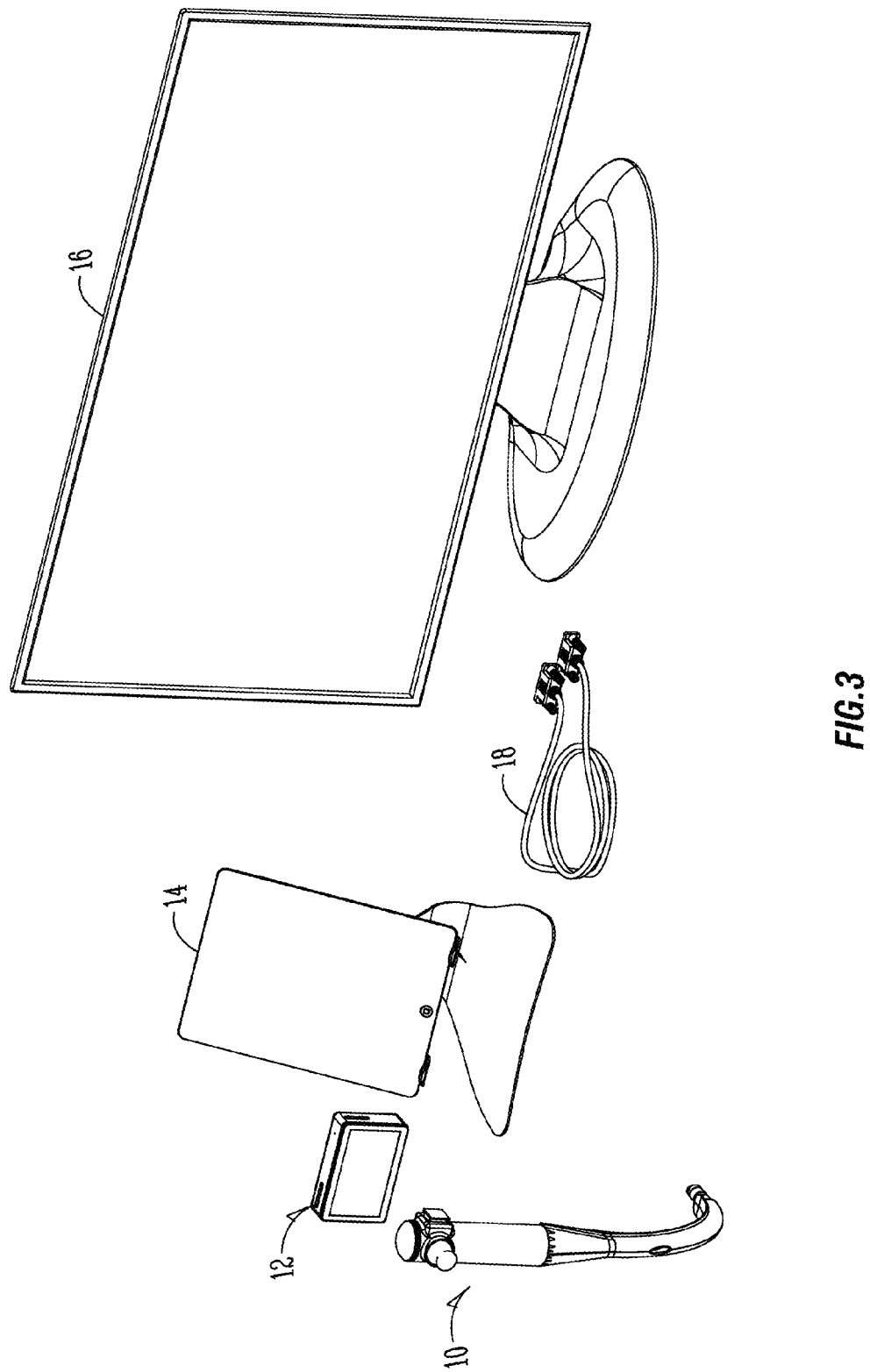
FIG. 3 is a high angle, right side, perspective 3D model view of the instrument of FIG. 1A and optional auxiliary touch screen monitor, iPad, touch screen monitor/television panel and cables.

Referring now to FIG. 3, in addition to interactive LED monitor 12, an iPad 14 (or other tablet form computer), touch screen monitor/television panel 16, cables 18, can optionally be other human interface components used with Guided Trachea Intubating Device 10.

FIG. 3 shows these components can be used for human interface with the mechanical articulation, stylet guidance and insertion, and interactive LED monitor. They may have responsive touch screen capabilities to provide guidance to the distal tip and be mounted to handle body or removed having signals provided via cabling, wireless or blue tooth technologies. An iPad and/or touch screen monitor/television panel may be utilized as the primary components for human interface with the Guided Trachea Intubating Device.

FIG. 3 illustrates device 10 and its monitor 12 could be used in association with other components. For example, a tablet computer 14 and large display 16 could be connected by appropriate cabling 18 (or wireless communication). This could allow recording of video taken by the onboard camera device 10 and/or visualization of the camera view on larger display 16.

Still further, instead of joystick control, touchscreen control at monitor 12, tablet 14, or even perhaps display 16 could be programmed so that the user could swipe on any of those screens to instruct the direction and amount of change of orientation of working end 90.

Such components are readily commercially available. Ability to calibrate touchscreen control to commensurate distal tip movement is possible in a number of ways.

Solenoids

Figure 10:
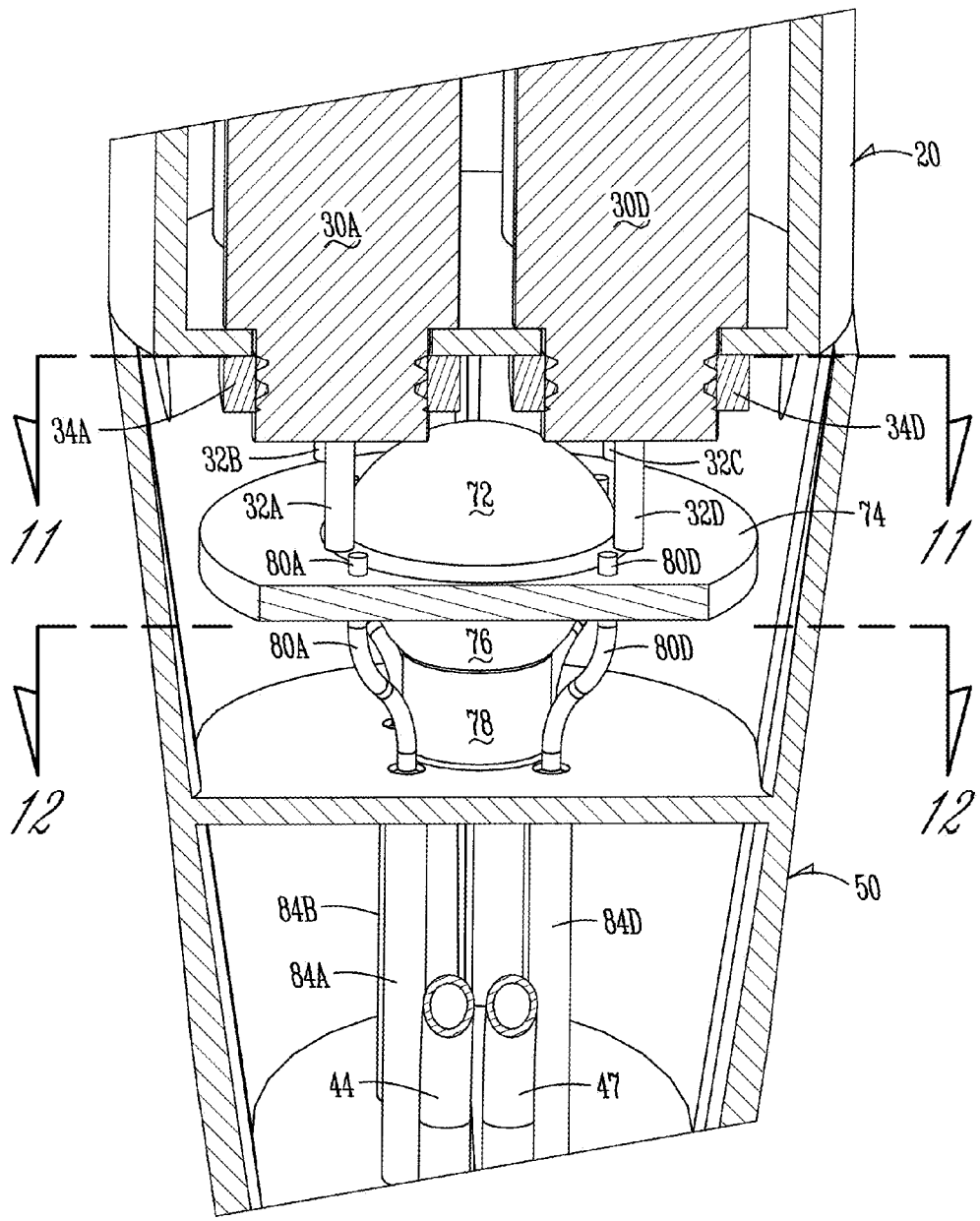
FIG. 10 is an enlarged sectional view taken along line 10-10 of FIG. 9 illustrating attachment of wires to what will sometimes be called a gyro disk which can be manipulated by a set of solenoids in the handle.

Handle 20 includes four solenoids 30A-D and has an end wall with apertures through which the bottom of solenoids 30A-D and corresponding solenoid plungers 32A-D would extend. See FIG. 6. As indicated in some of the drawings, each solenoid 30 could have an external threading that would fit through a corresponding aperture in the distal end of handle housing 20. A nut can then be threaded to the underside of that end wall to clamp each solenoid in place. See solenoid nut mountings 34 in FIG. 10.

Solenoids 80 could be push or pull solenoids, which are relatively inexpensive and available from a variety of commercial sources. If push solenoids, one or more could push on disk 70 to tilt it. If pull solenoids, they could be attached to disk 70 and one or more could pull on disk 70 to tilt it. Alternatively, linear actuators could be used. They can push or pull.

Intubating Body

Referring now to the invention in even more detail, FIGS. 2 to 18A-B show the components responsible for mechanical interface and actuation of the distal tip by mechanical means of actuating the tip with swivel components/integrated light and camera using solenoid style "push-pull" method. Electric motors or electromechanical actuation are alternative options.

Intubating body 50 is attached to the distal end of handle 20 (e.g. by adhesive, sonic welding, fasteners, or other methods). It has a curved shape that can be selected according to desire or need for intended use; that is, correlated to the size and anatomy of a human air way when the patient is supine. Scale, form factor, amount of curvature can vary by design. Reference can be taken to certain of the incorporated by reference citations given herein for examples. In this embodiment, the length and curvature is selected for use with a variety of human patients. As shown in FIGS. 1B-E, distal working end 90 ends up basically at a 90° angle to handle 20 when in a home or reference position. However, this can vary according to need or design.

PCB solenoid control driver 36 manipulates gyro disk 70 via solenoids 30 and controls the articulation of the distal tip 90.

Gyro Disk

Figure 7A:
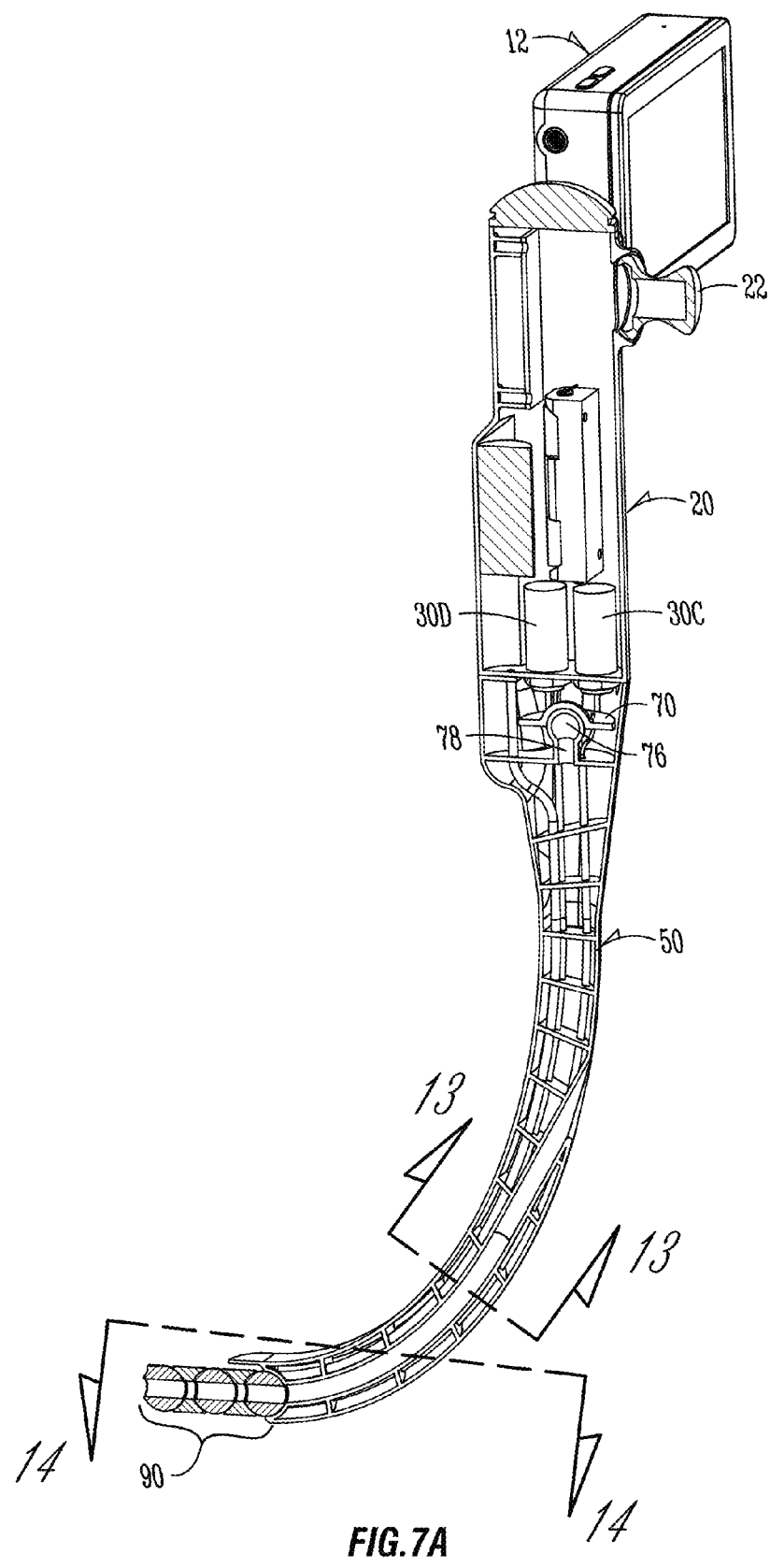
FIG. 7A is a sectional view of the entire device of FIG. 1A taken along line 7A-7A of FIG. 1C.
Figure 7B:
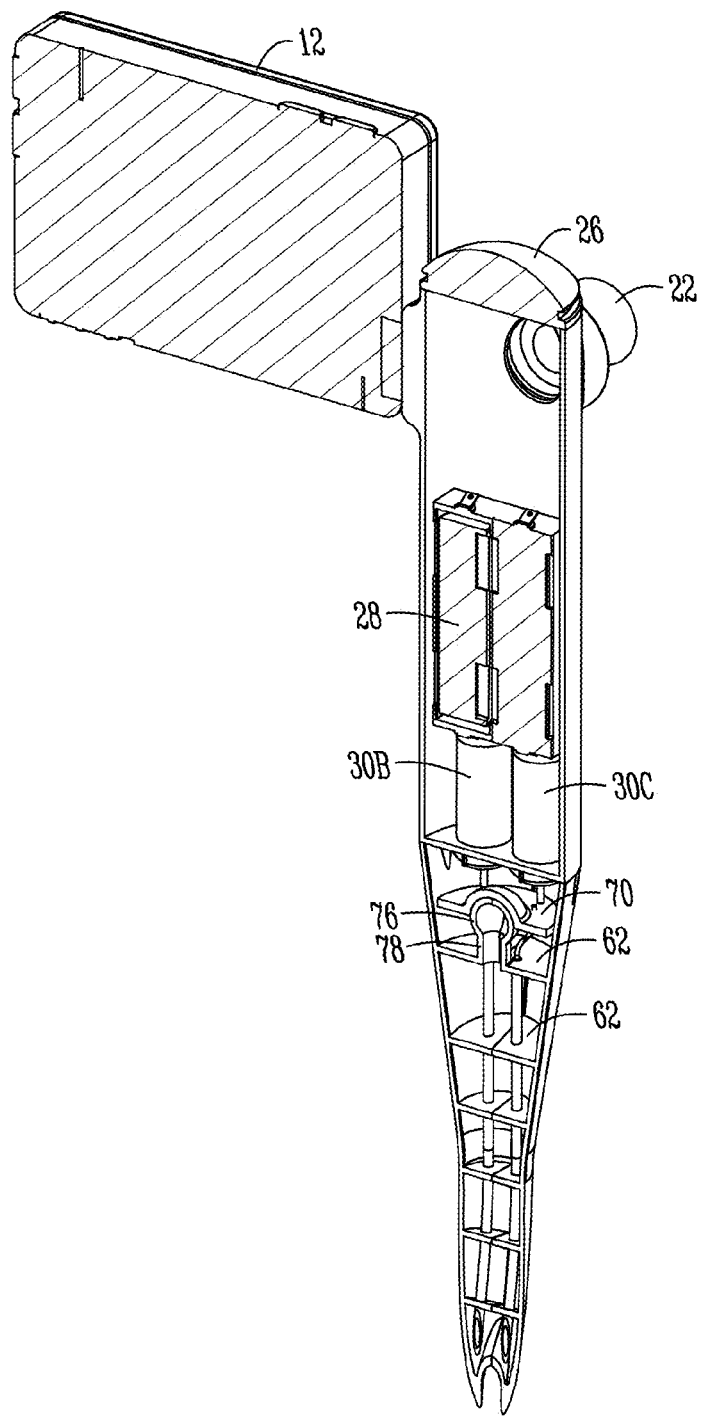
FIG. 7B is a sectional view of FIG. 1A from a different plane (see line 7B-7B of FIG. 1D).

What is called gyro disk 70 (FIGS. 4A-B) has a hemispherical central portion 72 and a radially outward extending flat plate 74. As shown in FIGS. 7A-B, ball-shaped support 76 is fixed on or into a cross support structural plate or wall 62 in body 50 and extends upwardly. Complementary cup or hemisphere 72 in the center of gyro disk 70 sits on top of ball support 76 (which is extended along a stem 78 from structural wall 62 in handle 50) and thus can tilt in any direction on ball support 76.

FIGS. 9-12 illustrate how solenoids 30 have their plungers 32 positioned basically at the four quadrants of plate 74 of gyro disk 70 on its top side. By appropriate programming of solenoid control board 36, movement of joystick 22 would be correlated to the actuation of none or up to four of the solenoids to control the tilting of gyro disk 70 in any direction within a range of movement on ball support 76.

FIGS. 1A-E show that this unified device 10 therefore has a user-proximal work handle end 20 that would remain outside the patient and that a portion of intubating body 50 and working end 90 would enter the patient. Materials for the components can be selected for biocapability, sterility, and other requirements such as are needed or desired for such medical applications. The user would grab handle 20 with thumb up and at joystick 22. Display 12 would be in direct line-of-sight of the user. Distal working end 90 could be lowered and pointed into the patient's mouth and oral cavity. The on-board camera would allow the user to roughly position distal end 90 relative the patient's vocal chords. A stylet opening in body 50 (see reference number 66, FIG. 1C) is available to the user.

FIG. 2 shows instrument 10 of FIGS. 1A-E partially exploded and with the left side housing covers of handle 20 and intubating body 50 removed (and not shown) to show internal components and their cooperation.

Stylet entry point 66 provides entry to a guided pathway 64 internal of body 50 to the distal tip 90 for further articulation prior to insertion (see FIG. 4A).

Intubating body 50 halves (right 52 and left 54) can be made from medical grade engineering plastic as injection molded parts which may be any color or translucent and may be autoclavable or disposable. Likewise can other components, such as vertebral structures 92, and 96-99, handle housing (left and right), joystick 22, and cap 26.

Distal End Vertebral Structures Manipulatable by Wires

The distal end 90 of device 10 will be described in terms of vertebral structure in the sense that the combination can flex in various directions like a human spine does with its vertebra. Balls 92, 97, and 99 (referred to as intervertebral joints) alternative with ring-shaped components 96, 98 (called vertebral bodies). The distal ends of wires 80 extend through guide tubes 84 in body 50 and through aligned passageways through all the components of 90, and are attached to distal-most ball 92 (see FIGS. 18A and B). FIG. 2 shows vertebral members 92, 96-99 separated from one another and wires 80 threaded through them. When finally assembled, members 92, 96-99 are cinched into abutment with wires 80 per FIGS. 18A-B.

FIGS. 7A-B show additional detail regarding the interior of device 10 including the stylet channel 64 (FIG. 7A) and examples of guide tubes 84A-D for wires 80A-D (FIG. 7B).

Figure 9:
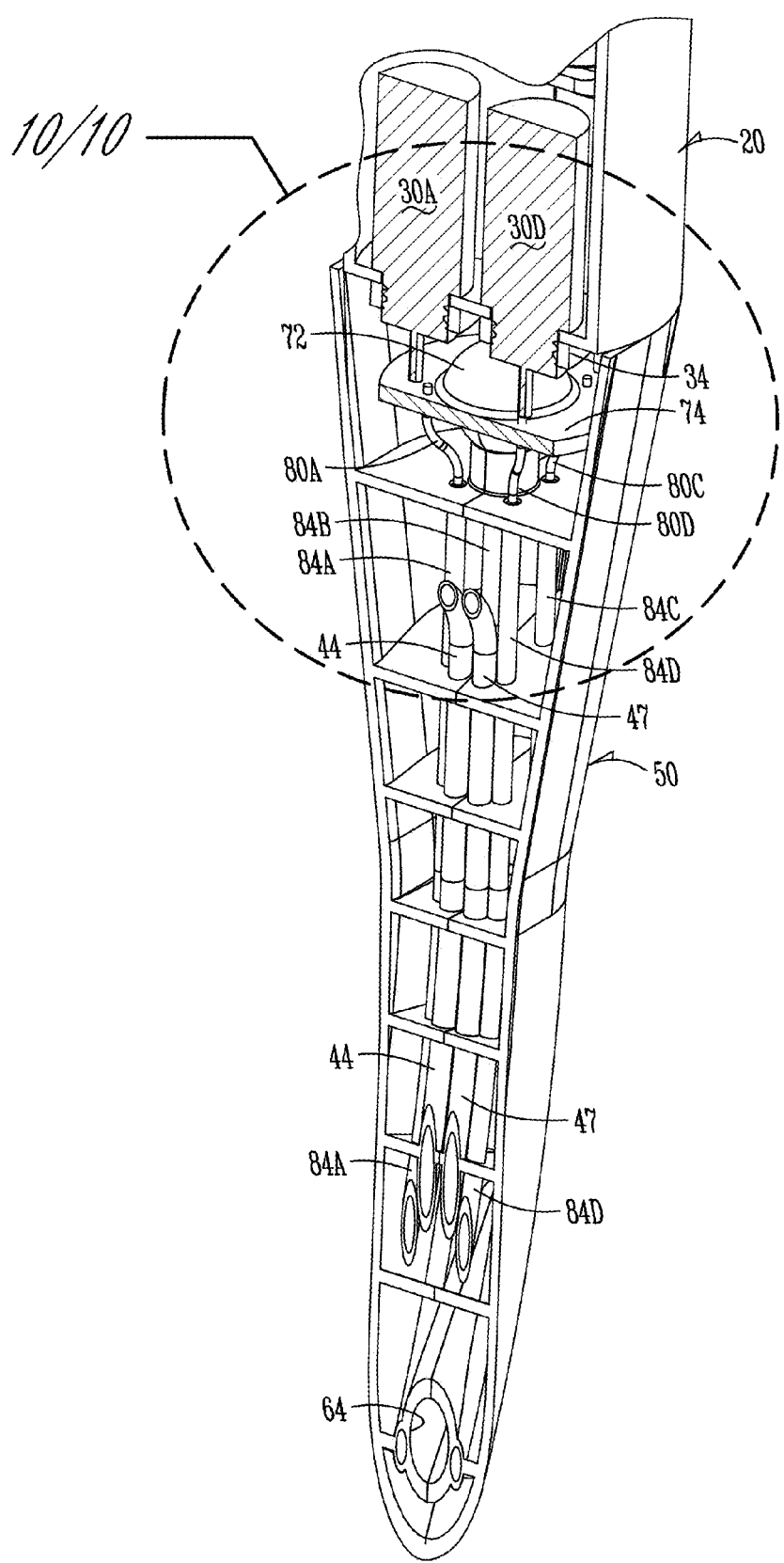
FIG. 9 is an enlarged sectional view showing components in the handle and part of the body of the device of FIG. 1A (see line 9-9 of FIG. 1D).

FIG. 9 gives additional details regarding disk 70, wires 80A-D, guide tubes 84A-D, guide tubes 44, 47, and the orientation of the solenoids 30A-D relative to disk 70.

The various sectional views beginning at FIG. 7A through FIG. 18B give additional detail of how wires 80 attach to gyro plate 70, how wires 80 are guided through the length of intubating body 50, how the wires attach to and hold the vertebral structures of tip 90 against the distal end 58 of intubating body 50, how the fiber optics of camera 40 and LED 41 are routed to distal end 90, and how a central stylet pathway 64 exists from the side of intubated body 50 to the very distal end of distal vertebral structure 90.

The guided wires promote smooth and accurate articulation of the vertebral distal tip 90 as each wire 80A-D slides within its own complementary tube 84A-D in response to tipping or tilting of gyro disk 70. The user thus gets responsive control of tip 90 articulation from the proximal end of instrument 10.

2. Operation

Figure 11:
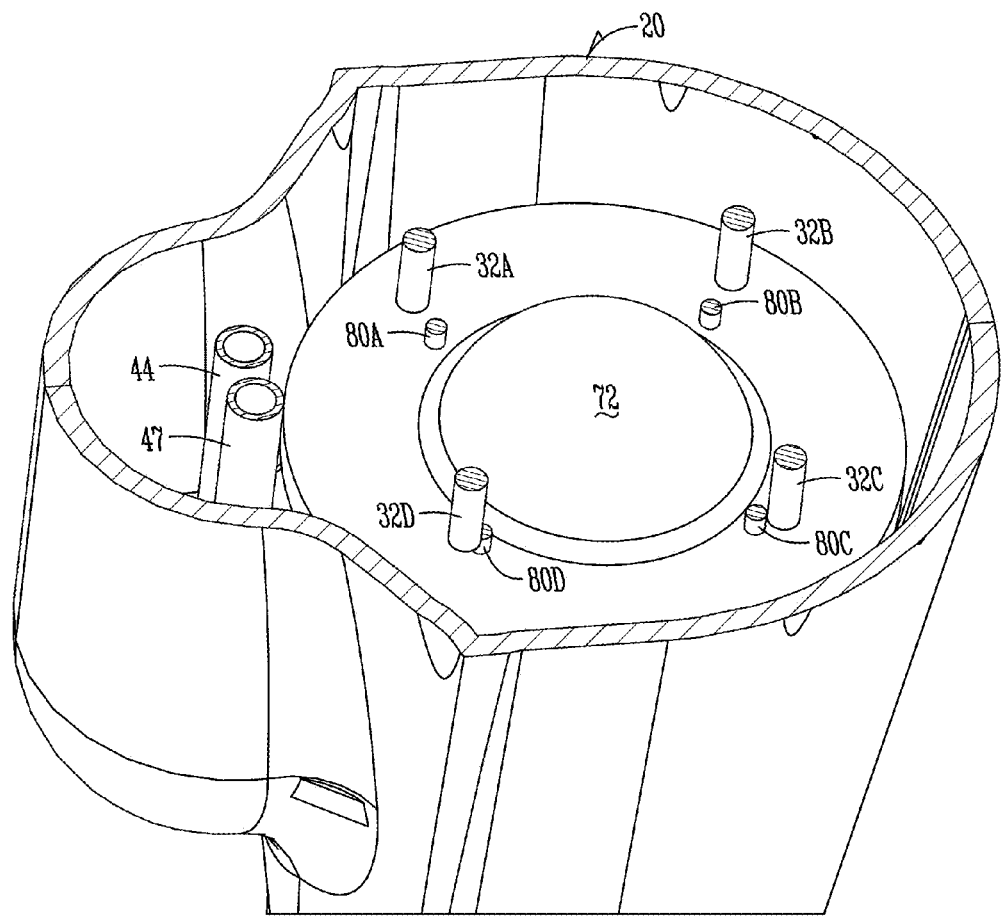
FIG. 11 is a sectional view from a different angle of the gyro disk, attached wires, and solenoid plungers (see line 11-11 of FIG. 10).
Figure 12:
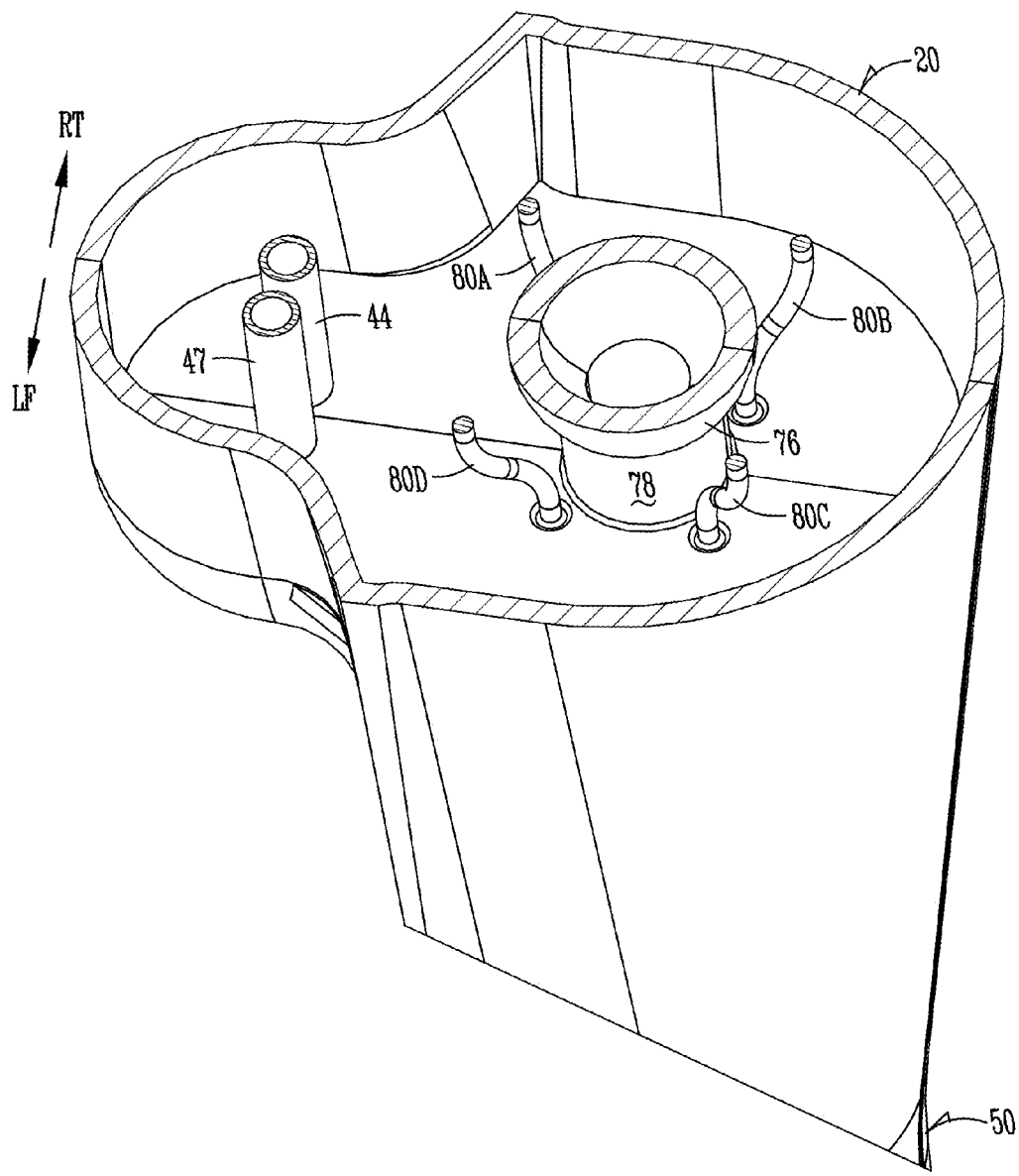
FIG. 12 is a sectional view underneath the gyro disk illustrating how the wires are threaded into guide tubes into the scope body (see line 12-12 of FIG. 10).
Figure 13:
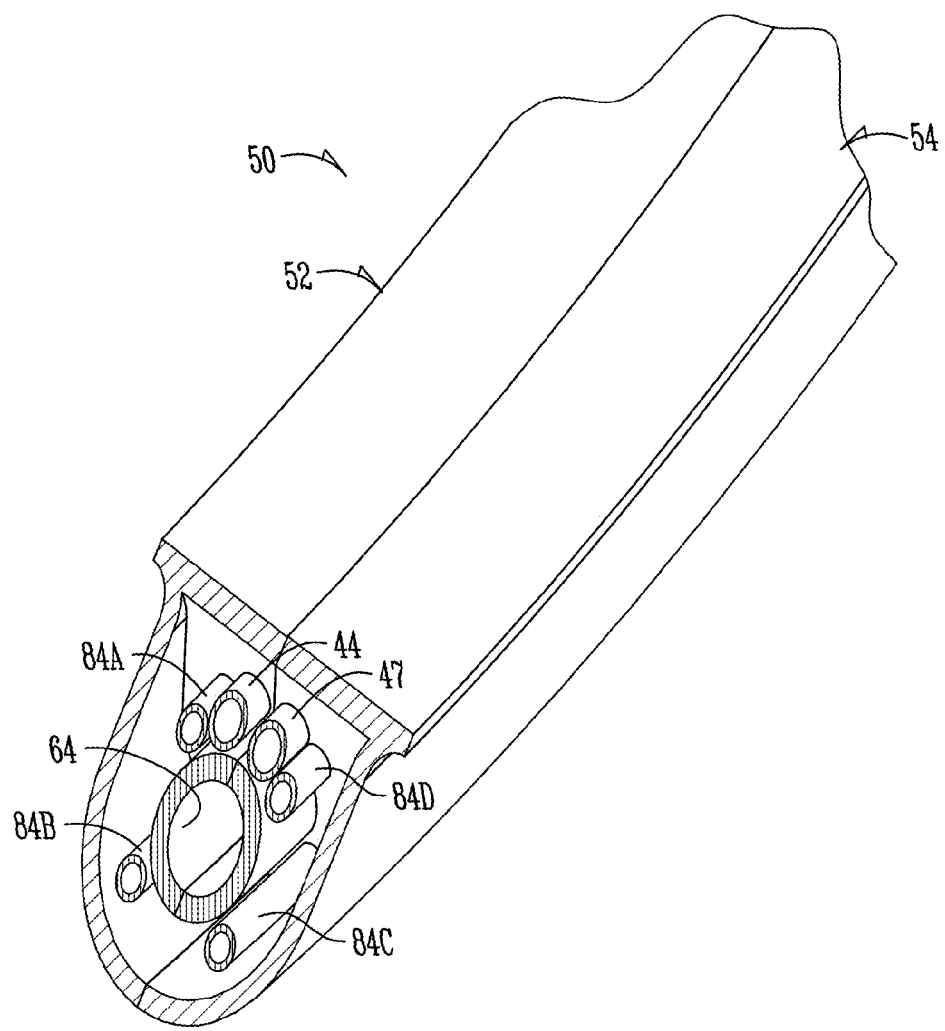
FIG. 13 is a sectional view along the scope body illustrating the guide tubes for both the wires and fiber optics for the camera and illumination source, as well as a central stylet channel (see line 13-13 of FIG. 7A).

By appropriate selection of length of wires 80 relative to the longitudinal length of body 50, the vertebral pieces 92, 96-99 are pulled into serial abutment and against a cupped receiver 69 at the distal end 58 of body 50 (see FIG. 4C) and the proximal ends of wires 80 are attached to gyro disk 70 (FIG. 11). Gyro disk 70 pivots on top of pivot ball 78 which is fixed in body 50 (see FIGS. 9-12). In this manner, wires 80 ties vertebral pieces 92, 96-99 together like a spinal cord. Because wires 80 are flexible but resist deformation along their longitudinal axis, pieces 92, 96-99 are held in abutment but can bend over at least a range of movement in different directions, like a human or animal spine or vertebrae. The direction and amount of bending depends on the direction and amount of tilting of gyro disk 70 on its pivot ball 78.

Vertebral members 92, 96-99 have aligned central bores which form the terminal portion of stylet pathway 64. Thus, the trajectory out of distal opening 68 of pathway 64 of a stylet that would be threaded into inlet opening 66 along body 50 (see FIG. 2) could be adjusted with at least two degrees of freedom movement. In other words, tip 90 could be moved up, down, left, right, or other orientations relative to an orthogonal plane relative to the distal end of intubation body 50 to give the operator of instrument 10 high flexibility to adjust that tip 90 relative to body 50. Importantly, not only can tip 90 by adjusted in those different general directions, the spinal nature of tip 90 also means the tip bends or curves increasingly relative to amount of deflection from home or straight out position. The position in space of outlet opening 68 can be changed by tilting disk 70, but the vertebral pieces 92, 96-99 would rotate or slide relative to one another to create curved exit paths or trajectories 67 (see FIGS. 19A-C) out of stylet path 64 (when adjusted away from what will be called the home position when disk 70 is basically horizontal in the context of FIG. 7A). A curved path would provide a curved guided trajectory of a stylet threaded through path 64 and out of distal exit opening 68. This can allow a wider range of possible reach of the stylet as it will exit along a more diverging curved path than a linear one from outlet 68.

The way in which user adjustment of tip 90 is effectuated is as follows.

Solenoid plungers 32 could have two positions (fully retracted and fully extended). If so, extension of just one solenoid plunger allows four different full tilts of plate 74 in four orthogonal directions. But operation of two solenoids at the same time would allow four additional full tilts in-between the four single solenoid actuations. Thus, plate 74 could be fully tilted in essentially eight different directions. For purposes of analogy, if the four solenoids 80A-D were considered positioned at northeast or NE (solenoid 80A), southeast or SE (80B), southwest or SW (80C), and northwest or NW (80D) relative to the plane of plate 74, and wires 80A-D were attached at similar positions on plate 74, plate could be tilted at any of those four points by actuation of the corresponding single solenoid at that position. But if two solenoids are actuated concurrently, tilting could occur at four more points on disk 74. Actuation of NW solenoid 80D and NE solenoid 80A, disk would tilt in a north or N direction (between NW and NE). Actuation of NE solenoid 80A and SE solenoid 80B would tilt disk 70 in an east or E direction, and so on. As can be appreciated, in this configuration (where solenoid plungers 32 can only be fully retracted or fully extended, compare retracted at distance D1 in FIG. 4B versus extended distance D2 in FIG. 4B), solenoids opposite one another would not be concurrently operated.

If solenoid plungers 32 can be controlled to variable extended lengths, the adjustability of vertebral distal end 90 would be increased. For example, a single solenoid plunger could be extended only partially (not to its fully extension) and cause a fraction of tilting of disk 70. This would move end 90 a fraction of its possible range in a correlated single direction. Likewise with partial extension of two adjacent solenoid plungers. But different amount of extension of two adjacent plungers would result in almost infinite variation in correlated movement of tip 90 relative to a plane orthogonal to the distal end of body 50. In other words, instead of being limited to N, NE, E, SE, S, SW, W, NW, any direction in the entire 360 degrees could be possible. For example, full extension of NE solenoid 80A and ½ extension of SE solenoid 80B would result in a tilt in the general direction mid-way or ½ between NE and E. Full extension of NE solenoid 80A and ¼ extension of SE solenoid 80B would result in a disk tilt closer to NE than ½ between NE and E. If solenoid plungers 32 are basically infinitely adjustable in length, almost infinite tilt directions of plate 74 around its 360 degrees are possible.

Variable extension or stroke solenoids are commercially available. An example is described in U.S. Pat. No. 5,138,291 which is incorporated by reference herein. The amount of extension or stroke of the solenoid plunger is proportional to the driving current supplied to the solenoid. Control board 36 would be configured to translate user tilting of joystick 22 into a correlated actuation of one or more solenoids 80. As can be appreciated by the foregoing description, depending on the capabilities of board 36 and the nature of solenoids 80, there might not be a precise 1:1 correspondence in joystick movement relative to disk 70 tilting. But it can be correlated at least as to rough direction in four directions (if not more). This would provide at least four alternative adjustments of end joint 90 in orthogonal directions.

As shown in FIGS. 7A, B and 8-14, tubular guides 84A-D, corresponding with wires 80A-D, support and guide those wires from attachment at four quadrants of plate 74 of gyro disk 70 (see FIGS. 10, 11) down to working end 90.

As will be appreciated, the vertebral structure of working end 90 is illustrated in FIGS. 14-18A,B. It is basically a multi-piece joint having five serially abutting elements 92, 96, 97, 98, 99 that can move relative to one another. When they are assembled as in FIGS. 14, and 18A,B, and when the four wires 80A-D are attached to distal component 92, there is a fixed length between the proximal ends of wires 80A-D fixedly attached to gyro disk 70 and their fixed attachment into channels 94A-D and end intervertebral joint 92. Such fixation can be by interference fit, adhesion, soldering, welding, some type of fastening, or other methods.

As shown in FIGS. 8-12, wires 80A-D bend towards the longitudinal axis of body 50 to enter their guide tubes 84A-D. Wires 80A-D can be made of any material which can perform these functions. One example would be a metal such as stainless steel. Each wire 80 could be a single strand. It is possible they could be multi-strand. As mentioned previously, each wire 80A-D for these purposes is essentially not deformable along its longitudinal axis but has some ability to flex. The forces needed to be applied to disk 70 to move end effector 90 as a stylet guide, even if end effector 90 comes into contact with patient anatomy, should not be more than a fraction of a foot-pound. Therefore, many materials for wires 80 would likely suffice. Some plastics might be possible.

Thus, when assembled, gyro disk 70 can only tilt on ball support 76 but by appropriate selection of length of the wires relative to device 10, including the vertebral structure 90 and attachment of wires 80A-D to that last distal vertebrae section 92, tilting of gyro disk 70 in a distal direction would push on at least one of the wires 80A-D. This would then push on the corresponding side of end vertebrae 92. Tilting of disk 70 in that manner would pull on any opposite wire 80. That combination would cause end effector 90 to curve away from the direction of tilt of disk 70. Solenoid plungers 84 act as mechanical stops against over-tilting of disk 70.

Because of the connection of wires 80A-D between disk 70 and end vertebral joint 92, the wires pass through the entire end of body 50 and end effector components 96, 97, 98, 99 and hold them all in abutting positions. Thus, the pushing and pulling of four wires 80A-D by the extension of plungers 32A-D of solenoids of 30A-D on the top of disk 70 allows any amount and angle of orientation of end effector 90.

Figure 14:
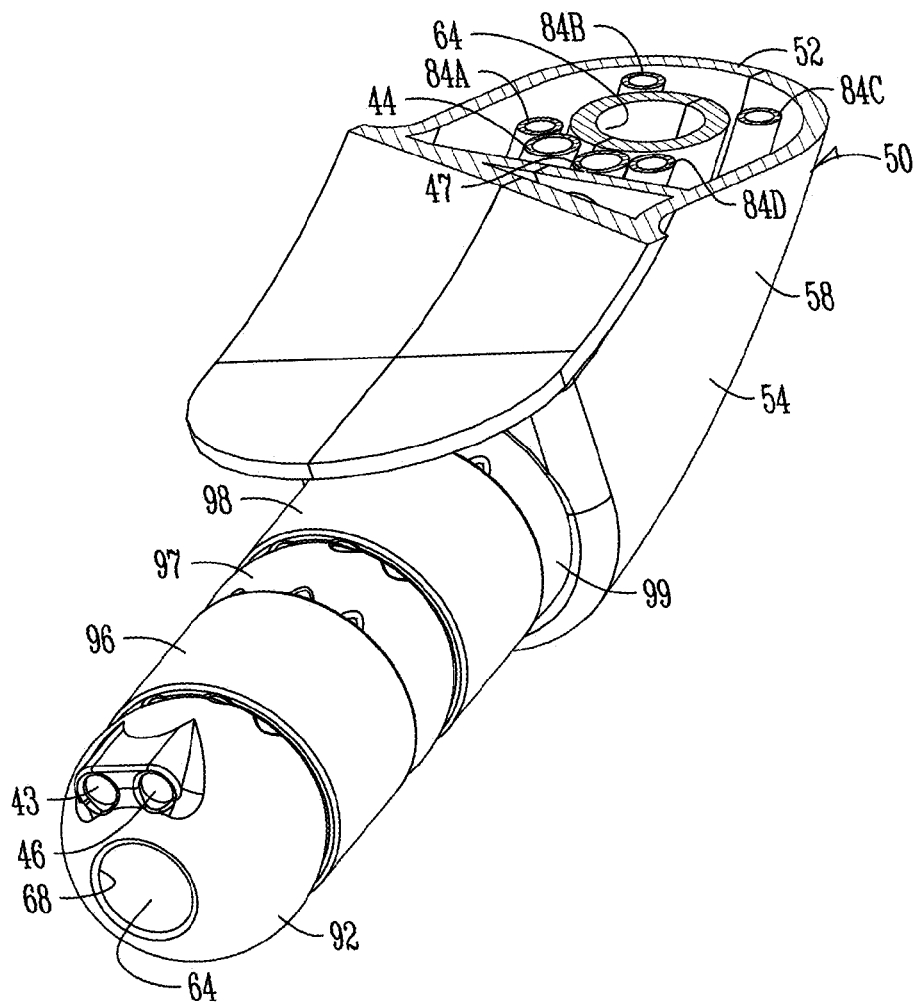
FIG. 14 is an isolated and partial sectional view of the distal working end of the device of FIG. 1A showing the continuation of the guide tubes and stylet channel as well as the very distal opening for the stylet and camera and illumination lenses (see section line 14-14 of FIG. 7A).
Figure 15A:
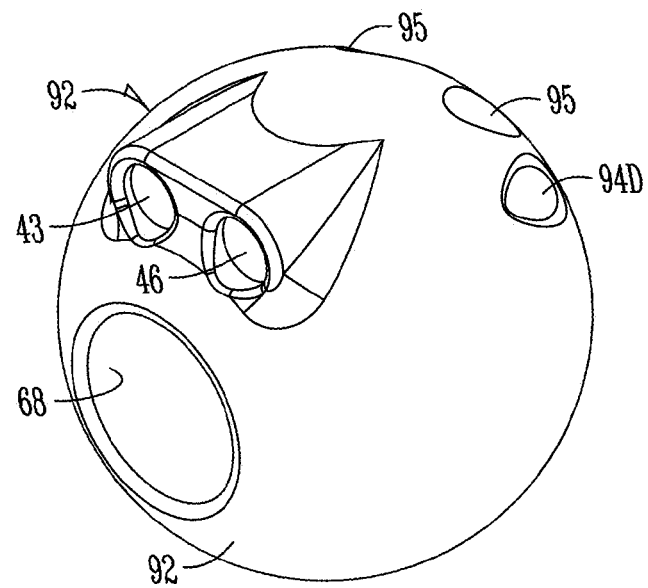
FIG. 15A is an enlarged perspective view of the most distal component of a manipulatable vertebral-column-like combination that comprises the manipulatable distal working end or stylet guide in this embodiment.
Figure 15B:
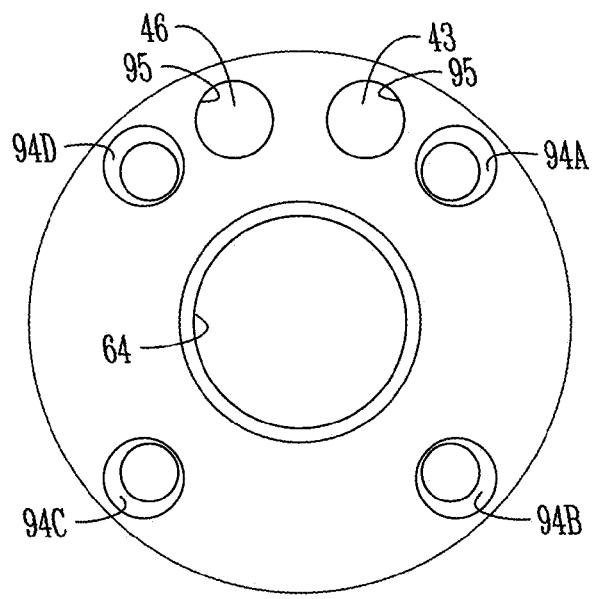
FIG. 15B is a back plane elevational view of FIG. 15A.
Figure 16:
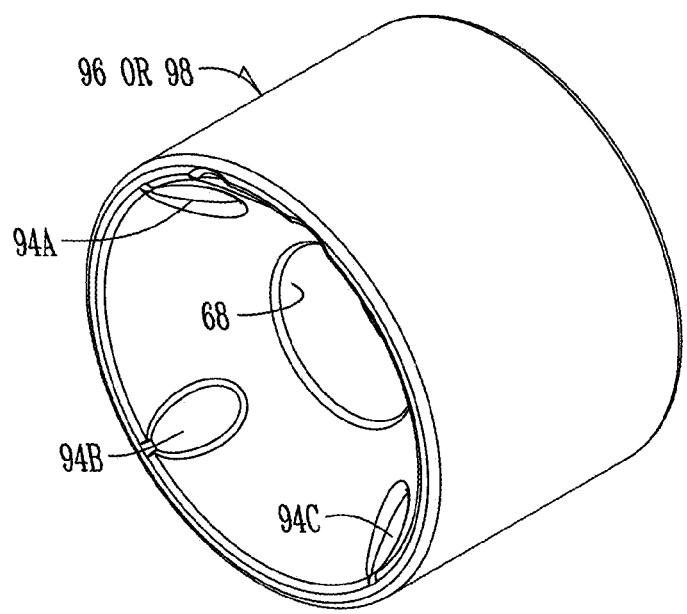
FIG. 16 is an enlarged perspective view of a vertebral body used twice in the working end of FIG. 14.
Figure 17:
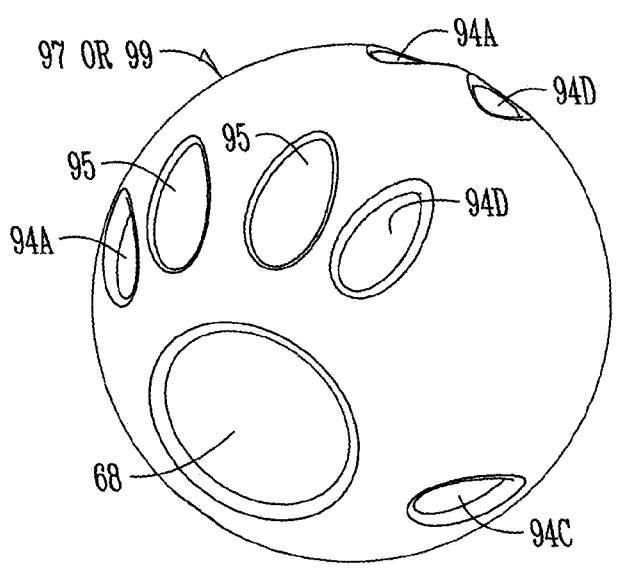
FIG. 17 is a perspective view of an intervertebral joint used twice in the working end of FIG. 14.
Figures 19A, 19B, 19C:
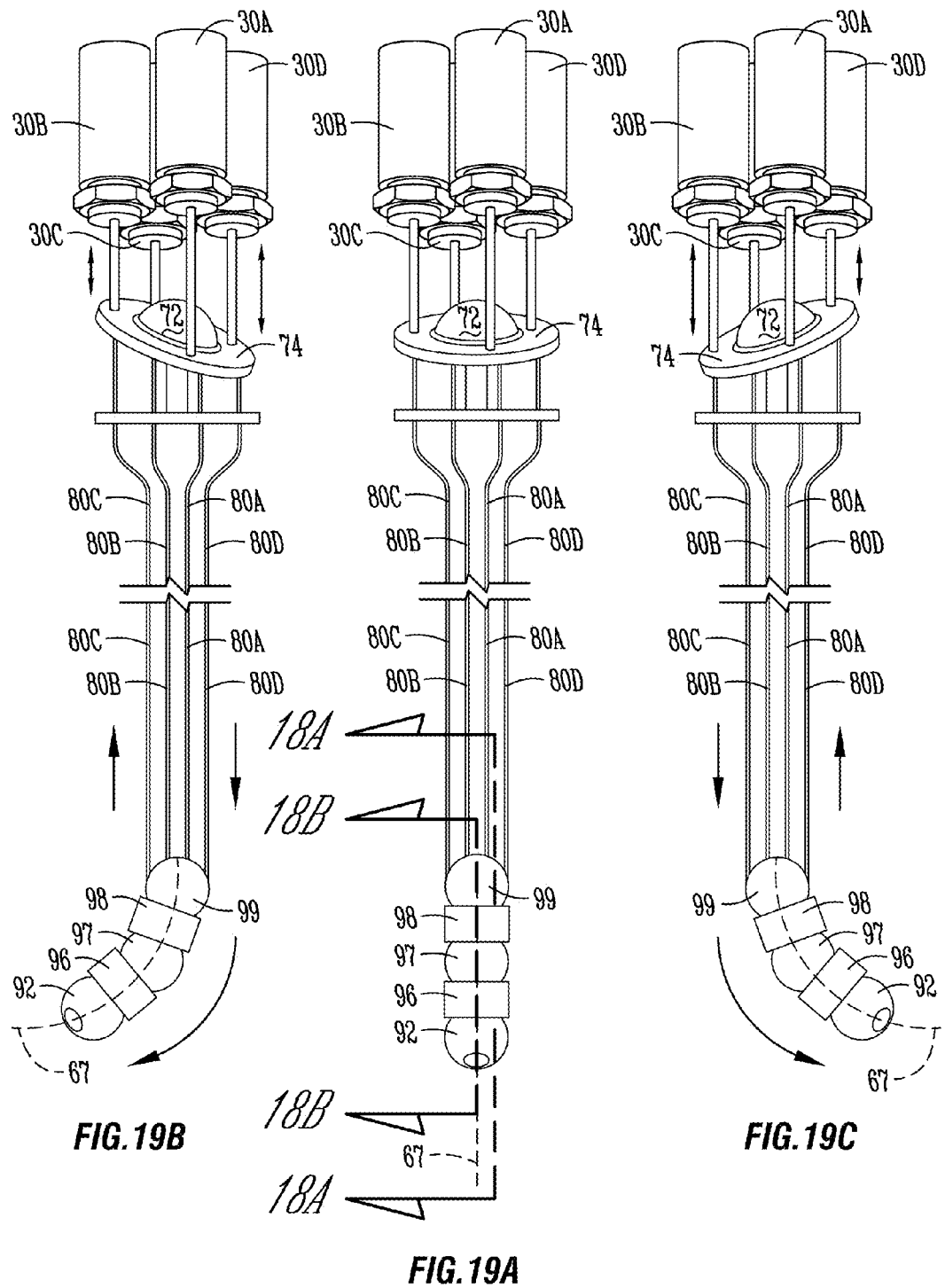
FIG. 19A is a diagrammatic depiction of the distal vertebral-like assembly, the wires up to the gyro disk, and solenoids of FIGS. 2 to 18A-B in a home or reference position.
FIG. 19B is a diagrammatic view showing how elongation of at least one of the solenoids tilts the gyro disk, pushes or extends at least one of the wires, and causes movement and changed orientation of the working end relative to the home position. The changed orientation of the distal end of the instrument essentially is a stylet guide that allows change in exit position and trajectory of a stylet that can be threaded through the stylet channel.
FIG. 19C is similar to FIG. 19B but shows a different solenoid elongating and the different reaction of the working end.

FIGS. 19A-C show this concept diagrammatically. FIG. 19A shows the components in what will be called a home or reference position. No solenoid plunger 32A-D is extended and gyro disk 70 is basically in a horizontal position on ball support 76 as instrument 10 is basically vertical. Vertebral structure 90 would thus basically extend straight out horizontally from cupped receiver 69 holding intervertebral joint 99 at the distal end of intubation body 50 (as shown in FIG. 14). The exit trajectory 67 for a straight end 90 would be horizontal. In other words, like shown in FIGS. 18A, B, all of the components of end effector 90 would be along an axis substantially in a single plane.

However, the tilting of disk 70 would cause the pushing and pulling in opposite directions (see FIG. 19B). This would cause a curling or changing in orientation of vertebral structure 90 in the direction of shortening.

Opposite pushing on disk 70 (FIG. 19C) would cause curling or change in orientation and in an opposite direction.

If solenoids 80 allow it, by adjustment of the amount of travel of each of the plungers 32A-D, not only can the end effector 90 be re-orientated in any of 360° direction from the distal end of device 10, the amount of re-direction can be regulated between just slight changes to an end of range of motion that would be inherent in the structure. As can be appreciated, the correlation between joystick movement 22 and solenoid activation can be by empirical methods.

Figure 4B:
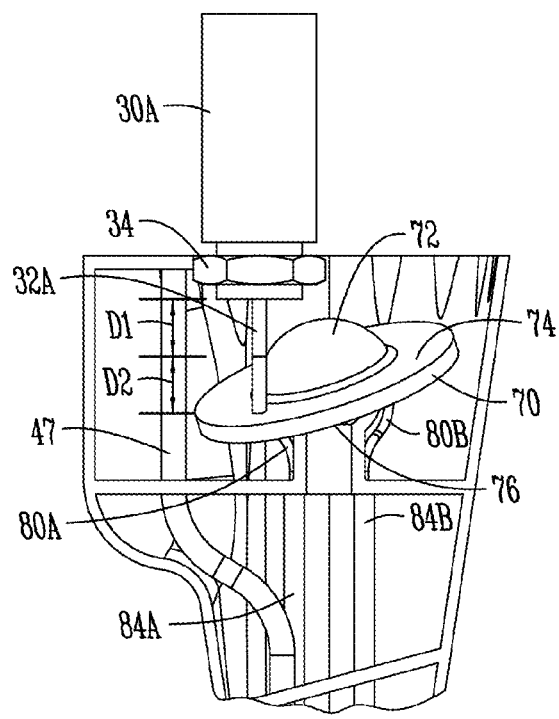
FIG. 4B is an enlarged isolated view of the proximal end of the body of FIG. 4A.
Figure 4C:
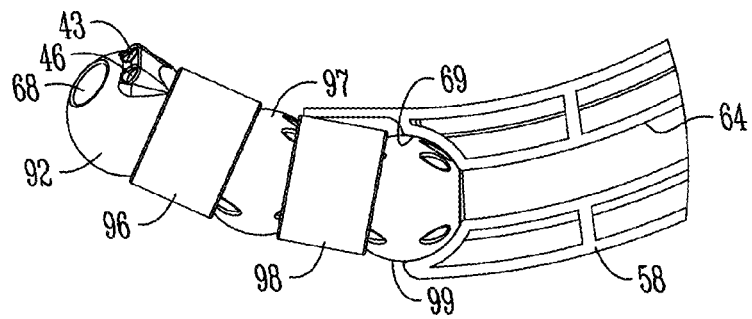
FIG. 4C is an enlarged isolated view of the articulating tip at the distal end of FIG. 2.
Figure 18A:
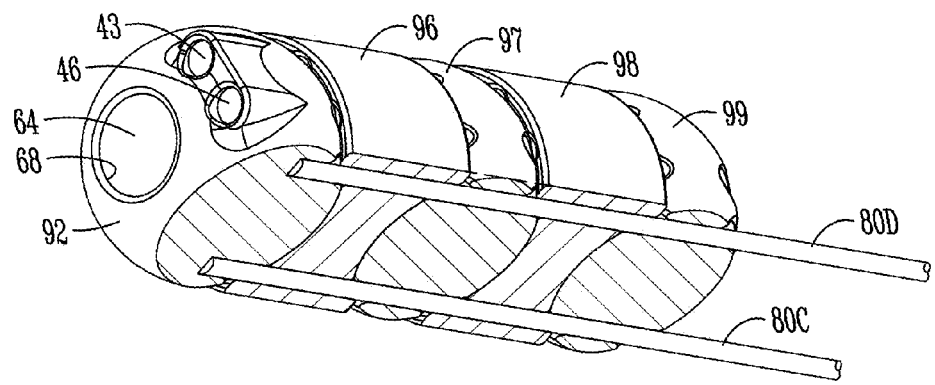
FIG. 18A is a perspective and partial sectional view of the combined intervertebral joints and vertebral bodies of FIGS. 17 and 16 that comprise the working end of FIG. 14 showing how the wires from the proximal end of the instrument extend to and are attached to the distal-most intervertebral joint (see section line 18A-18A of FIG. 19B).
Figure 18B:
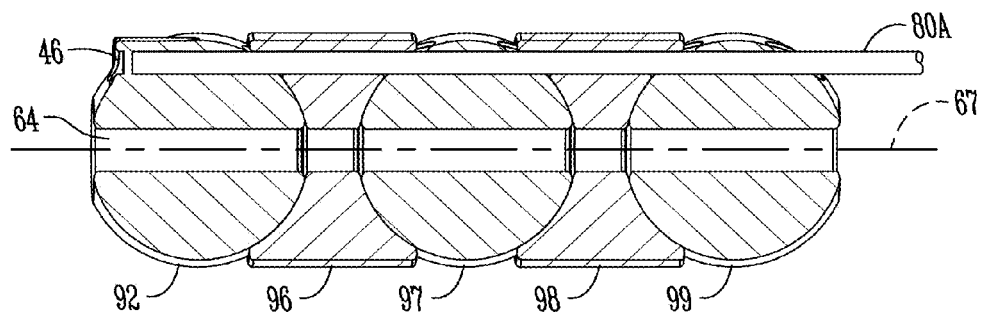
FIG. 18B is a side elevation of FIG. 18A from a different sectional plane showing one wire through the working end and showing the central stylet channel which can be changed in orientation (see line 18B-18B of FIG. 19B).

FIGS. 4A-C illustrate this concept with regard to one solenoid 30A. Together they show how tilting of disk 70 in one direction causes commensurate re-orientation of tip 90. These figures also diagrammatically indicate how stylet 65 can be inserted into opening 66 in the back side of body 50, and how stylet central channel 64 extends through body 50 to the vertebral structure 90. FIG. 18B shows that stylet channel 64 is maintained throughout the entire vertebral assembly 90 to an outlet 64. Thus, stylet 65 could be inserted in inlet 66, threaded through channel 64 and out of end 68 in the trajectory of the end effector 90 that has been instructed by the user. Stylet guide 65 thus provides a guide for an intubation tube 63. This can be threaded over the stylet 65 by methods well-known in the art.

C. Embodiment 2

1. Apparatus

Figure 21A:
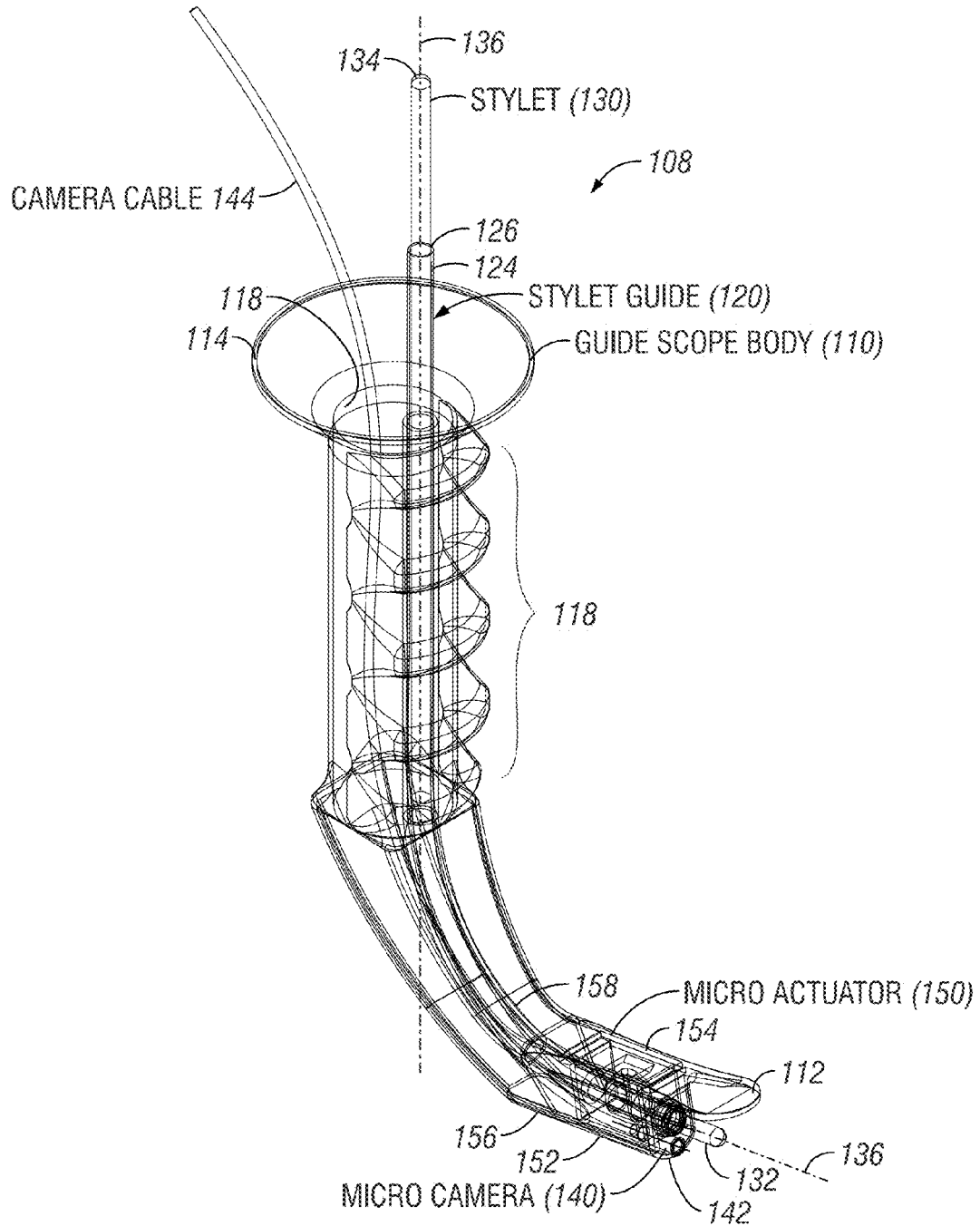
Figure 21B:
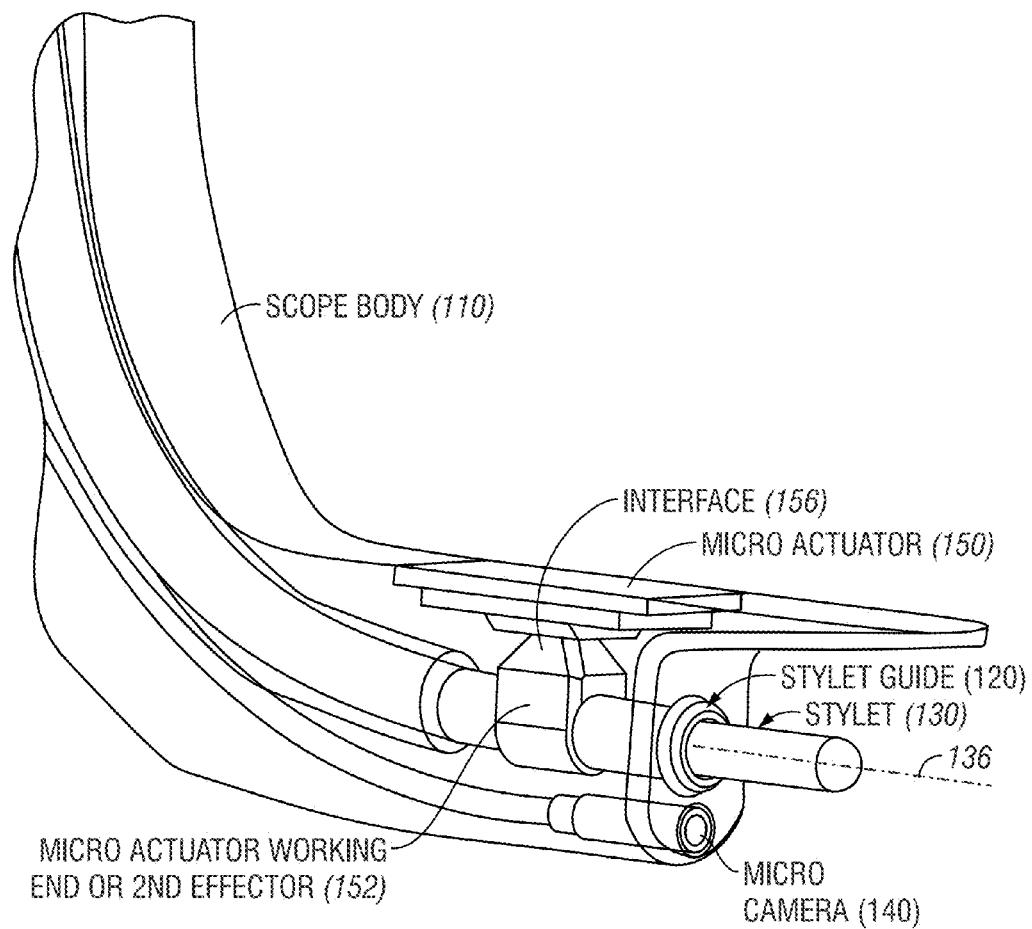
Figure 22:
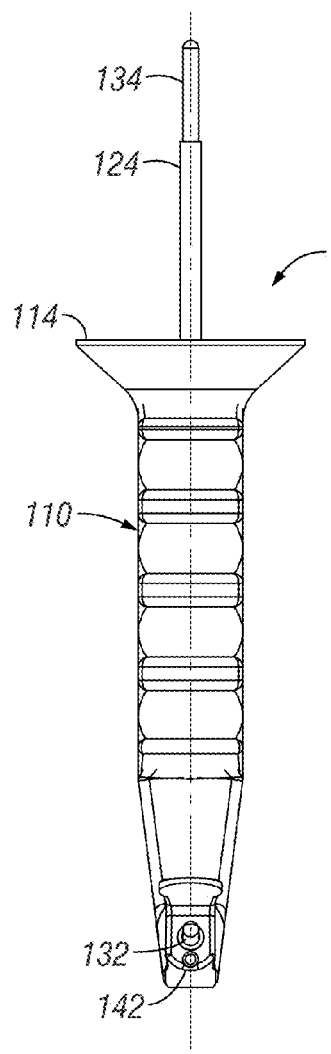
FIG. 22 is a front elevation of FIG. 21A.
Figure 23:
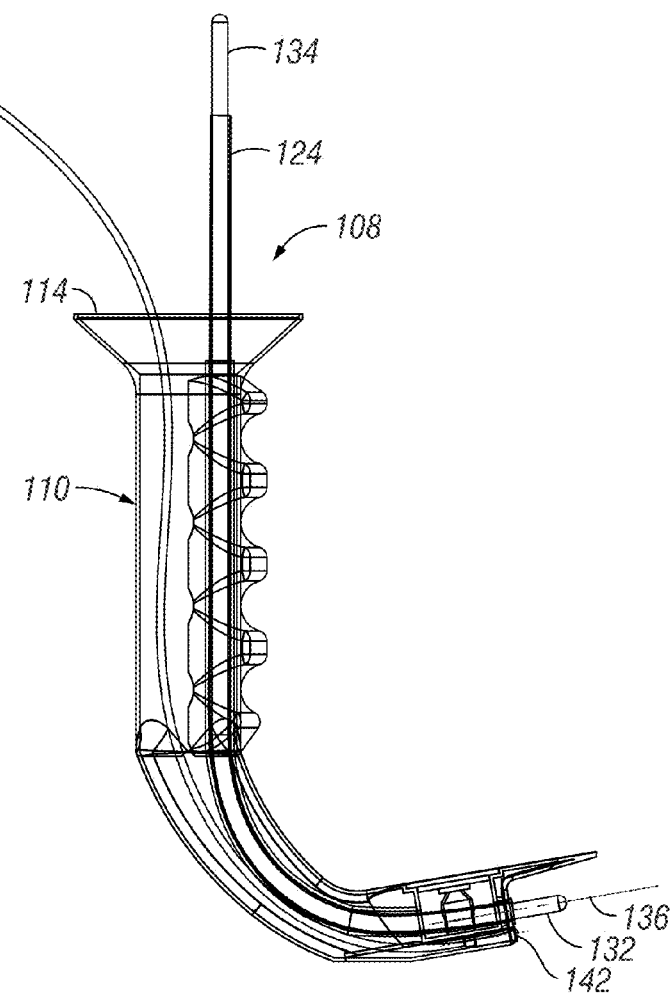
FIG. 23 is a wire-frame side elevation of FIG. 21A.
Figure 24:
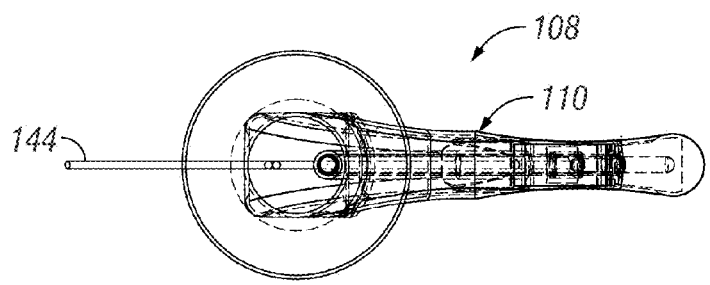
FIG. 24 is a wire-frame top plan view of FIG. 21A.

FIGS. 21A-C to FIG. 25 illustrate in various views a laryngoscope assembly 108 according to another exemplary embodiment of the present invention. As indicated in FIG. 21A, a scope body 110 includes a proximal open end 114 through which a camera cable 144 can be inserted to connect such cable 144 to a micro camera 140 at the distal end 112 of the scope body 110. The proximal end opening 114 also receives a stylet guide 120 that extends through the longitudinal bore of the scope body 110 to right at or near its distal end 112. A stylet 130 can thus be inserted and threaded axially through the stylet guide such that it can be moved out of the distal end of the scope body along a guided pathway determined by the orientation of the distal end of the stylet guide. This can serve as a guide over which an endotracheal tube can be advanced into the patient. The orientation and/or shape of the distal end of the stylet influences the trajectory or path of the endotracheal tube in the patient.

Figure 25:
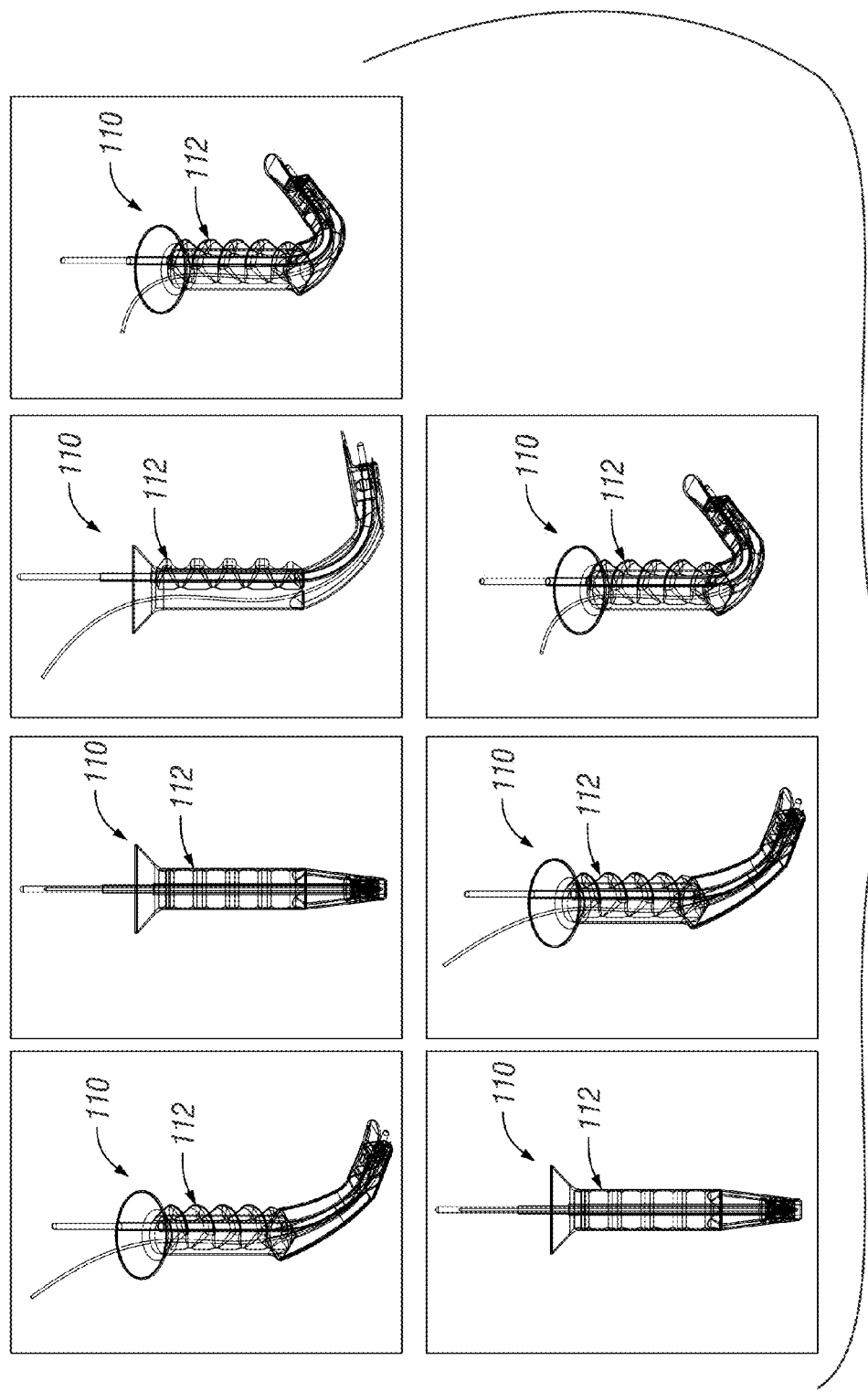
FIG. 25 is reduced-in-size wire-frame perspective views of the laryngoscope assembly of FIG. 21A from varying viewing angles.

FIGS. 21A-C to 24 show one example of the general shape and proportions of the scope body 110. FIG. 25 provides additional views of the distal end of the scope body. But that shape can vary according to design or need. That shape can be selected by the user according to their professional judgment of specific needs for a patient. For example, there could be an inventory of different scope body 110 shapes at hand and available for selection by the physician. Alternatively, the physician may prefer to use one shape.

FIGS. 21A-D also illustrate a micro actuator 150 can be built into the distal end 112 of scope body 110. Here it is described as a micro actuator because it is integrated into the scope body 110 and is relatively small in size. It is to be understood it is an actuator in the sense it supplies and transmits a measured amount of energy, force, or movement to another mechanism or system (here it translates an electrical instruction signal into physical adjustment of distal end 122 of stylet guide 110, see FIG. 21D). As shown, micro actuator 150 has a working end 152 (or end effector) that is operatively connected to at or near distal end 122 of stylet guide 120 (here working end 152 surrounds distal end 122 of stylet guide 120—see FIG. 21B). By compliant or non-compliant mechanism, working end 152 of actuator 150 has at least one degree freedom of movement, and preferably two degree freedom of movement at least, such that it can adjust the angular orientation of distal end 122 of stylet guide 120 relative to a reference axis 136 (e.g., longitudinal axis of the longitudinal bore of scope body 110 at its distal end 112). In other words, with two degree freedom of movement, distal end 122 of stylet guide 120 can be panned or tilted in two planes orthogonal to the longitudinal axis of the bore of scope body 110 at its distal end 112. Doing so allows a range of angular offset from that axis 136 in any direction 360 degrees around that axis 136.

The concept is diagrammatically illustrated in FIG. 21C. The actuator body is fixed/integrated into the top side of distal end 112 of scope body 110. It is electrically connected via wires 158 to a control system 180 which sends electrical signals to actuator 150. Working end 152 of actuator 150 is at the end of an interface 156 from a pivot point at or in actuator body 154. The actuating mechanism or function allows remotely controlled pivoting or deflection of interface 156 in at least two degrees freedom of movement (this is diagrammatically illustrated by the arcs X' and Y' in FIG. 21C). Stylet guide 120 (shown by itself in FIG. 21D) is made of a flexible material allowing it to flex when actuator working end 152 moves. In reference or home position, distal end 122 of the stylet guide 120, and thus stylet 130 when it is at or passed through guide 120, are along axis Z in FIG. 21C. If scope body 110 is inserted into the throat of the patient and the physician decides that extension of stylet 130 along axis or path Z is the correct trajectory for stylet 130, the physician causes the stylet to slide forward (e.g. manually by pushing on its proximal end 134 outside the patient and outside proximal end 114 of scope body 110). Distal end 132 of stylet 130 would follow axis Z because distal end 122 of stylet guide 20 is aligned along axis Z. Thus the trajectory of stylet 130 is set to follow axis Z. If however actuator 150 swings actuator working end 152 to the side (e.g. in the direction of −X' in FIG. 21C), it would flex distal end 122 of stylet guide 120 in a similar direction. This would change the trajectory for stylet 130 towards the −X direction in FIG. 21C. By further example, if working end 152 of actuator 150 swung forward (e.g. toward +Y' in FIG. 21C) it would flex distal end 122 of stylet guide 120 up. The trajectory of stylet 130 would then be towards +Y in FIG. 21C. If working end 152 of actuator 150 was swung both towards −X' and −Y' in FIG. 21C, the trajectory of stylet 130 would be towards a direction between −X and −Y in FIG. 21C. As can be appreciated, two degrees freedom of movement of actuator working end 152 can provide almost any stylet trajectory in diagrammatic cone that projects on the X/Y plane in FIG. 21C. Of course if the actuator working end 152 pivots about a fixed pivot point, it may not translate into identical corresponding change in exit trajectory for stylet 130 (translation of arcuate motion of actuator working end 152 does not have one-to-one translation geometrically to the X/Y plane in FIG. 21C). But there would be correlation that could be empirically determined or mathematically calculated. In this example, actuator working end 152 could be fixed to stylet guide 120 or it could slide along stylet guide 120.

As can be appreciated by one skilled in the art, actuator 150 could be any of a variety of types including, but not limited to, electromagnetic, electromechanical, electrostatic, piezoelectric, fluid, or thermal. Actuator 150 takes an electrical instruction signal and moves actuator working end 152. As will also be appreciated by those skilled in the art, the movement of actuator working end 152 could be one degree freedom (e.g. just in the X plane or just in the Y plane in FIG. 21C), or two degree freedom (e.g. in both the X and Y planes), or even three or four degrees freedom.

In any event, in this embodiment, the actuator 150 and working end 152 are integrated into the scope body 110 such that they do not materially alter the outside dimensions of the scope 18 at that portion.

One example of a micro actuator is described in U.S. Pat. No. 6,469,415 which is incorporated by reference herein. It describes a relatively small form factor that can translate electrical signals into forces that can move structures in certain directions. This is by example only one type of small motor or actuator that can be remotely controlled to cause adjustment or movement of a structure. Other examples are described in U.S. Pat. Nos. 7,924,514 and 8,223,461, incorporated by reference herein.

Figure 27A:
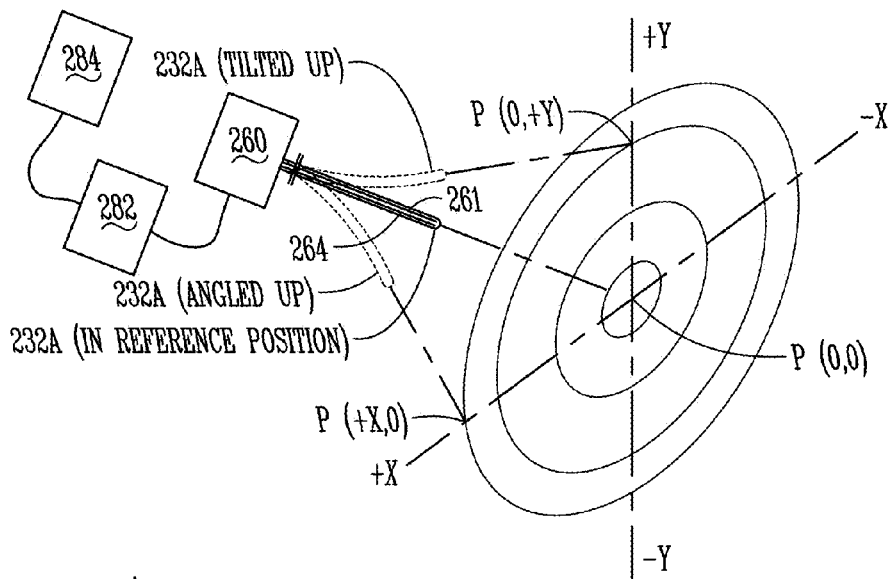
FIGS. 27A-C are diagrams illustrating a still further third alternative embodiment according to the invention, where the distal end of the stylet itself can be changed in angular orientation or shape. In one example, four wires or strips are placed in radially spaced-apart positions along the longitudinal axis of at least the distal portion of the stylet (e.g. equally spaced at 90 degrees apart). The stylet is made of a flexible material. One or more wires or strips can be pulled or pushed, or lengthened or shortened, by activation instructed by the user at or beyond the proximal end of the instrument. By selective lengthening or shortening of one or more wires or strips, the distal end of the stylet can be bent away from a reference position (e.g. vertically, horizontally, or a combination). This would result in adjustment of its trajectory or path. An intubation tube could then be threaded over the stylet into position in the patient.
Figure 27B:
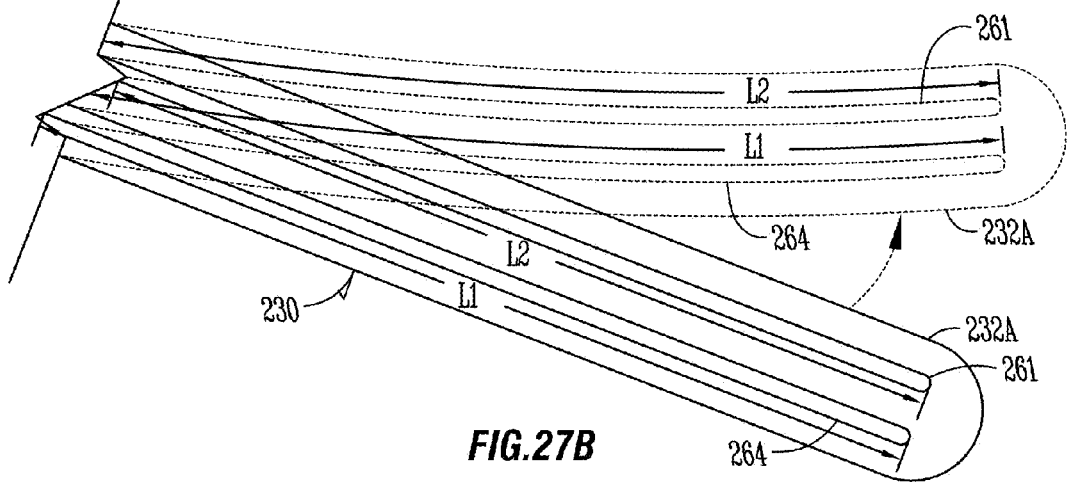
Figure 27C:
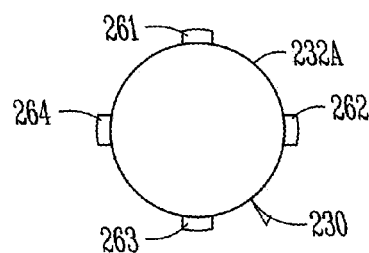

As schematically illustrated at FIGS. 27A-C, distal end 122 of stylet guide 120 can be moved in a range relative to the X/Z plane approximately plus or minus 15 (fifteen) degrees and in that the YZ plane approximately plus or minus 15 (fifteen) degrees. To accomplish this, the end 122 of stylet guide 120 is flexible (e.g., can be moved from a normal position by plastic deformation over the above range at least). It returns by resiliency to its normal position but this is not required. Materials that are possible include various plastics and silicones.

Micro actuator 150 would be a small device that could be encapsulated inside the laryngoscope. It could be part of the main body of the laryngoscope or a separate body which attaches together with the upper guide and tongue to create a laryngoscope. This motorized device body would be designed to snap together/interlock with the upper body. The tongue, the lead-in of the laryngoscope, could be a disposable unit or a unit which requires cleaning. A disposable latex-like sleeve with a spherical ball end could be attached to the inner tongue. The latex sleeve could be a separate item or part of the disposable tongue. The sleeve would be fed into and through the micro actuator extending to the top side of the main body. The stylet would then be fed down and through the latex sleeve. The spherical ball allows for free and controlled axial movement of the stylet by use of the micro actuator. Once the stylet is inserted and camera view is established the operator would zero that view as a "0" set point.

As can be appreciated, this combination shown in FIGS. 21A-C to 25 allows simultaneous visualization at and around the area in front of the distal end of the scope body 110 as well as the ability to alter the exit path and trajectory of a stylet 130 from the distal end 122 of the stylet guide 120. This allows good flexibility and control of operation of the laryngoscope assembly 108 by the user.

2. System

Figure 26A:
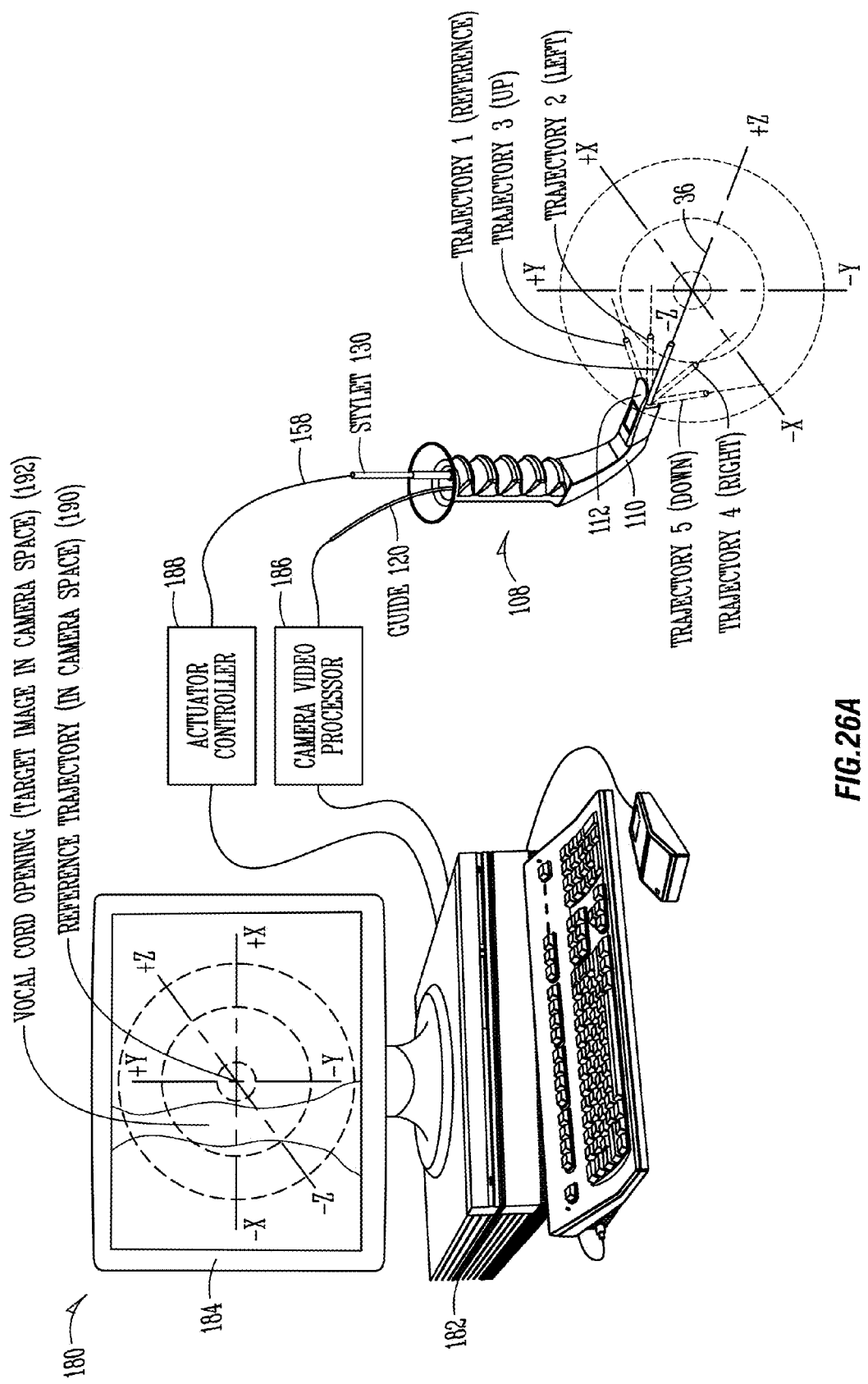
FIGS. 26A and B are schematic views of one way for at least two-degree freedom of movement control of the distal end of the stylet guide by the actuator of the assembly of FIG. 21A.
Figure 26B:
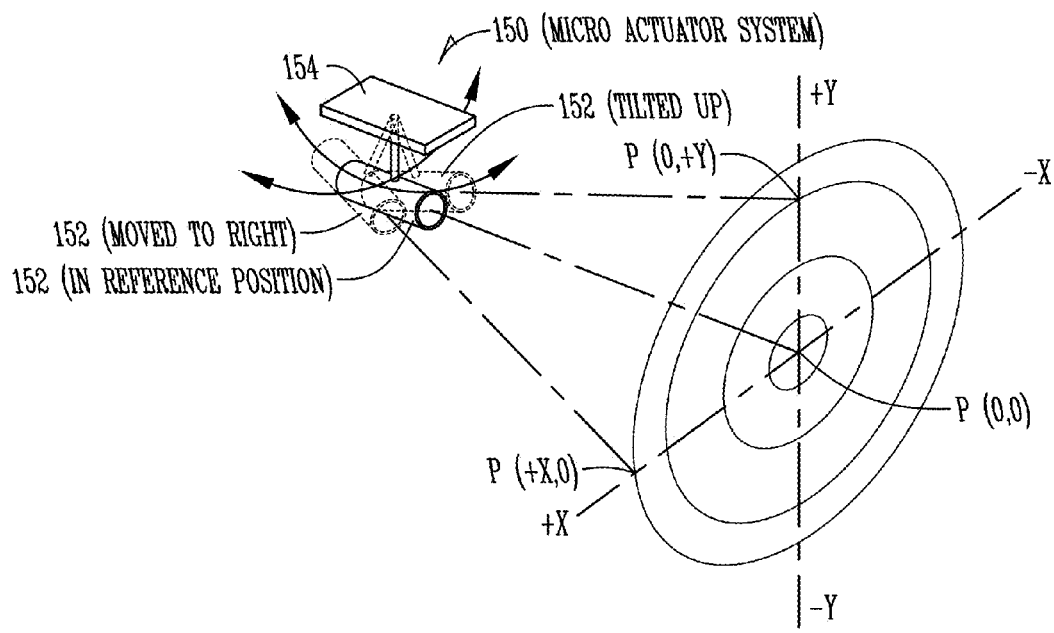
FIG. 26B diagrammatically illustrates how a micro actuator with at least two degrees of freedom of movement could change the angular orientation of the stylet guide.

FIG. 26 schematically illustrates how the assembly of FIGS. 21A-C to 25 can be operatively connected to a control system 180. A camera 140 can be connected to a video controller 186 or other interface to allow display of the field of view of the camera on the display 184 of the work station 182. An actuator cable 158 can be similarly directed through the scope body 110 and out its proximal end 114 to an actuator controller 188 or other interface to the computer or work station 182. The actuator controller 188 and/or work station 182 can include software that would allow a user to touch the display 184 such that the actuator controller 188 would translate that touched position to an offset from some reference position and instruct a pre-calibrated angular adjustment of the stylet guide 120.

For example, as illustrated in FIGS. 26 and 27, if a reference position for the normal coaxial position of the stylet guide distal end is right along the Z axis in the lower diagram of FIG. 27 or at the "reference position", virtually displayed on the display of FIG. 26, and once inserted the visualization of the patient's vocal cords shows an offset to a "target position" in virtual camera space of FIG. 26, software for the actuator controller would move or offset the angular direction of the distal end of the stylet guide proportionally to the offset shown between "reference position" and "target position" on the display screen of FIG. 26 by the trigger of the user touching the "target position" on the display of FIG. 26. That "target position" would correspond with the location of the desired path for the stylet relative to the patient's vocal cords, for example.

As can be appreciated, current technology of touch screens has many commercially available components that can be calibrated to translate a touch on a touchscreen into some instruction of movement relative to a reference position. See, e.g., U.S. Pat. No. 6,965,394 incorporated by reference, which describes such a touchscreen and its controlling hardware and software. The designer would select a controller and software that would interface with the micro actuator 150 and program it accordingly. U.S. Pat. Nos. 7,225,012 and 5,365,267, incorporated by reference herein, includes several patents or published patent applications which disclose various ways of robotic control of a surgical instrument.

The interaction between the touch screen and the controller would be through a set of programming and hardware, such as is common in the electronics industry. An example of the touch screen functionality is found at www.panji-touchscreens.com (having a U.S. contact address of PanJit Americas Inc., 2525 W. Huntington Dr., Tempe, Ariz. 85282). Included in the programming and hardware already available on the market for this purpose would be the ability to calibrate or "zero angle" the actuator. For those familiar in the art, this is akin to the "white balance" performed prior to every laparoscopic surgery. See, e.g., U.S. Pat. No. 5,365,267, and incorporated by reference herein for a discussion of "white balance".

U.S. Publication 2011/0319718, incorporated by reference herein, illustrates one form of the work station with display connected to a laryngoscope. Reference can be taken to some of that description regarding such a system. Likewise, U.S. Publications 2011/0270038 and 2010/0261967, incorporated by reference herein, provide some details of the same.

A feature of the embodiment of the invention is the ability of the user to control the angular orientation of the stylet guide and use a conventional stylet to better control placement of the distal end of the stylet relative to the patient's anatomy. This can be done with a touchscreen or other user interface controls.

3. Operation

Those of skill in the art can appreciate how the assembly and system described above would be operated and used on a patient.

Once laryngoscope 108 is placed properly in the patient's mouth, the operator will be able to visualize the pharyngeal anatomy, as is currently practiced. However, this laryngoscope 108 will also have an included stylet 130 that will be actuated (able to be redirected to any location seen on the display screen 184) from within the laryngoscope blade. The operator will simply touch the intended target on the display screen 184, and the actuator will respond, using a software translation of the touch instruction to actual physical manipulation of the stylet guide distal end 122 in correlation with the touch screen instruction (e.g. the camera space display of the anatomical area of interest through the camera in the scope body plus allowing the operator to adjust the stylet guide distal end angle by, for example, a touchscreen touch indicating direction of adjustment), to redirect the stylet to that location. The operator then advances stylet 130 through the vocal cord opening into the trachea. The stylet 130 remains in place while the laryngoscope unit is completely removed. An endotracheal tube (not shown) is then advanced over the properly positioned stylet, and the stylet is removed.

U.S. Pat. No. 7,169,155; Boctor, E. M., et al., "Virtual Remote Center of Motion control for needle-placement robots", Computer Aided Surgery, 2004, 9(5/6): 1-9, and Pham, M. T., et al. "Biomimetic steering robot for Minimally invasive surgery application, Advances in Robar Manipulators, In-Tech (ed.), 2010, pp. 1-25, all incorporated by reference herein, describe ways in which a working end can be remotely guided, including in the context of viewing on a display an image of the area around the working end (e.g. a needle or other surgical instrument) and translating the "camera space" relationship between working end and a target in the patient to causing some actual event at the location of the working end. These are meant to illustrate that image-based control can be implemented in many ways.

Extech Model BR240 Video Borescope/Wireless Inspection Camera available from Zefon International (see http://www.zefon.com/store/extech-br250-wireless-inspection-camera-video-borescope, incorporated by reference herein), is a commercially available video inspection tool that illustrates how a video camera of small form factor can be placed at the distal end of an elongated flexible tube or guide and communicate to a display at the remote operator a camera space view of what that camera "sees". An illumination source can also be operated at that distal end to provide illumination of the camera space.

This exemplary embodiment describes adjusting stylet trajectory from the distal end of the laryngoscope body by manipulating the distal end of the stylet guide tube. An actuator (in this first example towards the distal end of the stylet guide) has at least two degrees freedom of movement. This allows a certain amount of change of angular orientation of the distal end of the stylet guide relative some home or reference position. This, in turn, allows a range of adjustment of trajectory angle of a stylet extended out of the distal end of the stylet guide to allow the physician the ability to make adjustment to actual navigation of the stylet relative to the patient's anatomy. Fine control of the stylet independent of the end of the laryngoscope body distal end allows better navigation of intubation of the patient.

D. Embodiment 3

An alternative that may be preferred is diagrammatically illustrated at FIGS. 27A-C. FIG. 27A is similar to FIG. 26A in showing a distal end 232A of a stylet 230 which can be manipulated into different orientations relative to a home or reference position.

A main difference in this embodiment is that it is the stylet 230 that is adjusted in shape, not a stylet guide. As indicated at FIG. 27A, by curling, bending, angling, or otherwise altering distal end 232A, its trajectory or the path it would take in the patient's throat when it is extended into that throat can be varied.

In this example, stylet 230 is made of a material that is somewhat flexible. As indicated, see also FIGS. 27B and C, four wires or strips are radially spaced around the longitudinal axis of stylet 230 (here 90 degrees apart). As will be appreciated, if one of those wires or strips 261, 262, 263, or 264 were pulled proximally or the material of which they were made could cause them to shorten or contract longitudinally, it would cause stylet 230 to bend in that direction. If two adjacent wires or strips were pulled or contracted, it would cause stylet 230 to bend in a direction between those adjacent strips or wires.

Thus, if the wires or strips are like cables attached at or near distal end 232A of stylet 230, the direction and amount of bending of distal end 232A could be accomplished by mechanical or otherwise physically pulling one or more of those wires or strips. For example, a small linear motor or actuator could be instructed to do so by control system 260, 282, and 284. It could be calibrated for precise control. If the wires or strips could shorten or contract upon the influence of, for example, heat or electromagnetic field, by calibrated application of the same distal end 232A could be bent in a desired direction.

U.S. Pat. Nos. 8,182,418 and 6,858,005 describe examples of an elongated flexible cannula or guide that can be remotely controlled to change shape, including at its distal end. Examples of how the shape-change is affected including by electro-mechanical motors, pneumatic and hydraulic cylinders, pneumatic and hydraulic motors, solenoids, shape memory alloy wires, and electronic rotary actuators. This includes controlling shape relating to navigation within a patient's body.

U.S. Pat. Nos. 8,125,755, 6,468,203, 8,083,879, and 7,261,686 are examples of a few other elongated bodies, tubes, cannula, or guides that can be remotely controlled regarding some shape or form aspect, including in the context of manipulation or navigation in a patient's body.

These examples are provided to illustrate a few ways in which the stylet 230 of the exemplary embodiments might be controlled as to shape or orientation in the context of the laryngoscope. It is to be appreciated that there are a number of known technologies that could be applied to allow control of the distal end of a stylet from the distal end of a laryngoscope according to at least some of the aspects described above. The designer would take into account factors such as size, power, precision of control, features, etc. in selecting the way the stylet is adjusted in shape or form.

E. Options and Alternatives

As discussed earlier, the foregoing exemplary embodiments are exemplary only and not by limitation. Variations obvious to those skilled in the art will be included within the invention.

By way of a few examples, as indicated at FIG. 25, the shape of the scope body can vary according to desire and need. Likewise, the actuator in control of the stylet guide distal end can be through various methods and ways. It can be independent of having visualization through a camera or optical system. Also, user control of the actuator can vary and does not have to be touchscreen. There could be a joy stick or analogous control. There could even be foot or other tactile or manual control.

What is claimed is:

1. A system for intubating a patient comprising:
   a. an elongated curved intubation body having proximal and distal ends along a longitudinal axis and including a stylet pathway for threading a stylet therethrough to the distal end of the intubation body;

b. a handle at the proximal end of the intubation body;
c. a manipulatable stylet guide at or near the distal end of the intubation body aligned with the stylet pathway, wherein the stylet guide comprises an extension from the distal end of the intubation body that can be adjusted in orientation and curvature;
d. a camera vision subsystem providing an artificially illuminated field of view at or near the distal end of the intubation body;
e. an actuator subsystem operatively connected to the stylet guide to move the stylet guide in at least two degree freedom of movement in multiple directions from a reference position, wherein movement of the stylet guide from the reference position changes trajectory of the stylet pathway from the distal end of the intubation body, wherein the actuator subsystem comprises a set of elongated members along the extension and an actuator which can extend or shorten selected elongated members, wherein the elongated members comprise flexible wires;
f. a user interface subsystem operatively connected to the actuator and the camera vision subsystem, the user interface subsystem comprising:
  i. a manually operably control to instruct correlated movement of the stylet guide by the actuator;
  ii. a display to view the field of view of the camera vision subsystem; and
g. wherein the actuator subsystem further comprises a tiltable disk to which the flexible wires are attached and a component to tilt the tiltable disk in multiple directions in correlation to the manually operable control of the user interface subsystem.

2. The system of claim 1 wherein the extension comprises a series of abutting members which can move relative to one another and which include aligned apertures extending the stylet pathway to an distal outlet.

3. The system of claim 2 wherein the abutting members comprise a vertebral structure.

4. The system of claim 3 wherein further movement of the vertebral structure from the reference position increases curvature of the vertebral structure and increase divergence of the stylet pathway.

5. The system of claim 1 wherein the elongated members comprises shape memory alloy strips.

6. The system of claim 1 wherein the stylet guide comprises a stylet holder mounted in the intubation body which can support and guide a stylet, and which can be adjusted in orientation relative to the intubation body to change the trajectory of the stylet and its pathway.

7. A system for intubating a patient comprising:
a. an elongated curved intubation body having proximal and distal ends along a longitudinal axis and including a stylet pathway for threading a stylet therethrough to the distal end of the intubation body;
b. a handle at the proximal end of the intubation body;
c. a manipulatable stylet guide at or near the distal end of the intubation body aligned with the stylet pathway, the stylet guide comprising a set of abutting vertebral members;
d. a camera vision subsystem providing an artificially illuminated field of view at or near the distal end of the stylet guide;
e. an actuator subsystem operatively connected to the stylet guide to move the stylet guide in at least two degree freedom of movement in multiple directions from a reference position, wherein movement of the stylet guide from the reference position changes trajectory of the stylet pathway from the distal end of the intubation body, the actuator subsystem comprising a tiltable disk, a set of wires attached between the tiltable disk and the stylet guide; and an actuator that tilts the disk in any of plural directions;
f. a user interface subsystem operatively connected to the actuator subsystem and the camera vision subsystem, the user interface subsystem comprising:
  i. a manually operably control to instruct correlated movement of the stylet guide by the actuator;
  ii. a display to view the field of view of the camera vision subsystem.

8. The system of claim 7 wherein the user interface subsystem is carried on the handle.

9. The system of claim 7 further comprising an electrical power source in the handle for powering the actuator.

10. The system of claim 7 wherein the actuator comprises plural solenoids having extendable plungers aligned at spaced apart positions around the tiltable disk.

* * * * *